United States Patent [19]
Ma et al.

[11] Patent Number: 6,051,528
[45] Date of Patent: Apr. 18, 2000

[54] AMORPHOUS ALLOY CATALYST CONTAINING PHOSPHORUS, ITS PREPARATION AND USE

[75] Inventors: Aizeng Ma; Wanzhen Lu; Enze Min, all of Beijing, China

[73] Assignees: China Petro-Chemical Corporation; Research Institue of Petroleum Processing Sinopec, both of Beijing, China

[21] Appl. No.: 09/090,078

[22] Filed: Jun. 3, 1998

[30] Foreign Application Priority Data

Jun. 4, 1997 [CN] China ................................ 97 1 12305
Jul. 10, 1997 [CN] China ................................ 97 1 11955

[51] Int. Cl.[7] ...................................... B01J 21/02
[52] U.S. Cl. ......................... 502/207; 502/204; 502/202; 502/206; 502/208; 502/210; 502/211; 502/213
[58] Field of Search ..................... 502/202, 207, 502/208, 210, 211, 213, 204, 206

[56] References Cited

U.S. PATENT DOCUMENTS 4,478,871 10/1984 Sakaguchi et al. ........................ 427/34

FOREIGN PATENT DOCUMENTS 1073726 6/1993 China .

OTHER PUBLICATIONS

Applied Catalysis, 37 (1988) pp. 339–343 no month available.

Journal of Physical Chemistry, 97 (1993) pp. 8504–8511 no month available.

Journal of Catalysis 150 (1994) pp. 434–438 no month available.

ACTA Physico–Chimica Sinica, vol. 9, No. 3 (Jun. 1993) pp. 325–330 considered only to the extent of english abstract.

ACTA Chimica Sinica, 52 (1994) pp. 877–882 considered only to the extent of english abstract. No month available.

(source unknown) Sorption and Desorption on SiliCalite–1 (1994) pp. 91–793 considered only to the extent of english abstract. No month available.

*Primary Examiner*—Elizabeth D. Wood
*Attorney, Agent, or Firm*—Jones & Askew, LLP

[57] ABSTRACT

An amorphous alloy catalyst containing nickel and phosphorus comprising a porous carrier, a Ni—P amorphous alloy supported on the carrier, and a pre-supported catalytic component for inducing and catalyzing the formation of the Ni—P amorphous alloy onto the carrier. In a preferred embodiment, the catalyst contains 0.15–30 wt % of Ni, based on the total weight of the catalyst, 0.03–10 wt % of P, based on the total weight of the catalyst, 0.01–3.5 wt % of B, based on the total weight of the catalyst. The nickel exists in the form of Ni—P or Ni—B amorphous alloy, the atomic ration Ni/P in the Ni—P amorphous alloy is in range of 0.5–10, the atomic ratio Ni/B in the Ni—B amorphous alloy is in range of 0.5–10. The catalyst may further comprise from 0.01 to 20 wt % of a metal additive (M), based on the total weight of the catalyst. The metal additive (M) refers to one or more metal elements, except Ni, which can be reduced from the corresponding salt into its elemental form.

39 Claims, 9 Drawing Sheets

6,051,528

1

AMORPHOUS ALLOY CATALYST CONTAINING PHOSPHORUS, ITS PREPARATION AND USE

FIELD OF THE INVENTION

The present invention relates to an amorphous alloy catalyst, its preparation and use. In more detail, it relates to an amorphous alloy catalyst containing nickel and phosphorus, its preparation and use.

BACKGROUND OF THE INVENTION

The following two problems need to be overcome during the development of the amorphous alloy catalysts. One is how to increase the specific surface area of the amorphous alloy catalysts, so that the catalytic activity can be improved; the other is how to keep the catalyst in its amorphous state, i.e., how to enhance the thermal stability of the amorphous alloy catalyst. There have been numerous attempts to provide solutions to this problem.

In CN 1,073,726A, an alloy containing Al, rare earth elements (RE), P and Ni or Co or Fe was prepared by rapid quenching techniques. By alkaline leaching of Al from the alloy, using NaOH, a Ni/Co/Fe—RE—P amorphous alloy catalyst with high specific surface area of 50–130 $m^2/g$ was obtained. Its hydrogenation activity was greater than that of Raney Ni catalyst, which is widely used in industry. Such a catalyst exhibited the highest reactivity among all the prior art amorphous alloy catalysts reported so far.

An ultra-fine Ni—B amorphous alloy catalyst was reported by Deng et al., J. Catal. 150,434–438 (1994). This catalyst was prepared by adding 2.5 M aqueous $KBH_4$ solution dropwise, with stirring at 25° C., to an 0.1M nickel acetate ($Ni(CH_3COO)_2$) alcoholic solution. The resultant Ni—B deposit was first washed with 6 ml of 8M ammonium hydroxide ($NH_4OH$), and then with a large amount of distilled water. However, such ultra-fine Ni—B amorphous alloy particles exhibited poor thermal stability, although their specific surface area was as high as 29.7 $m^2/g$. Deng et al., also reported that ultra-fine Ni—P amorphous alloy catalyst can be prepared by heating an aqueous solution containing nickel acetate, sodium acetate ($CH_3COONa$), and sodium hypophosphite ($NaH_2PO_2$) at 90° C., and adjusting its pH to 11 with an aqueous solution of NaOH while stirring, and then sequentially washing the resulting deposit with ammonium hydroxide, and distilled water. The specific surface area of this Ni—P amorphous alloy catalyst is 2.78 $m^2/g$ only, while its maximal crystallization temperature increases to 394.4° C.

It was reported by Dichang et al., in Acta Physico-Chimica Sinica, 9(3), 325–330 (1993), that by introducing rare earth elements, such as Y, Ce and Sm, the resulting unsupported Ni—RE—P amorphous alloy catalysts exhibited a much better thermal stability than the corresponding unsupported Ni—P amorphous alloy catalyst. Similar results were also obtained by introducing La instead of the above rare earth elements, as reported in J. Chem. Soc. Faraday Trans. I, 82, 702 (1986).

The effects of the metal additives, such as Pd, Co, Cu, and Fe, on the hydrogenation properties of the Ni—B amorphous alloy catalysts were studied by Bingshi et al., as reported in Petrochemical Technology 23(2), 791–794 (1994). The results demonstrated that the addition of Pd could enhance the activity of the Ni—B amorphous alloy catalyst for cyclopentadiene hydrogenation, while other metal additives including Co, Cu, or Fe reduced the hydrogenation activity.

2

Chen et al., reported in Acta Chimica Sinica 52, 877–882 (1994) that an unsupported Ni—W—P amorphous alloy catalyst can be prepared by heating an aqueous solution containing nickel acetate $Ni(CH_3COO)_2$, sodium acetate ($CH_3COONa$), sodium hypophosphite ($NaH_2PO_2$), and sodium tungstate ($Na_2WO_4$) to 90° C., and adjusting its pH to 10–11 with aqueous NaOH with stirring, and sequentially washing the resulting deposit with ammonium hydroxide, distilled water and anhydrous ethanol. The Ni—W—P catalyst has a higher cyclopentadiene hydrogenation rate compared to a Ni—P catalyst, and has a lower cyclopentene hydrogenation rate than that of a Ni—P catalyst.

An Ni—P amorphous alloy catalyst supported on silica was reported by Jingfa & Xiping in Appl. Catal. 37, 339–343 (1988). The catalyst was prepared by chemical plating, i.e., by mixing a solution containing sodium citrate ($Na_3C_6H_5O_7$), nickel sulfate ($NiSO_4$), sodium hypophosphite ($NaH_2PO_2$), and sodium acetate ($CH_3COONa$) with a silica gel carrier, heating to 363° K with stirring, and keeping the pH at 5.0 for about 2 hours. The product was then washed with distilled water, and dried overnight. Such a supported Ni—P amorphous alloy catalyst exhibited not only a high specific surface area up to 85 $m^2/g$, but also a superior thermal stability (maximal crystallization temperature is 352° C.). However, such a supported Ni—P amorphous alloy catalyst exhibited the following disadvantages:

(1) This catalyst is prepared by mixing a $SiO_2$ carrier with a solution containing $Na_3C_6H_5O_7$, $CH_3COONa$, $NiSO_4$, and $NaH_2PO_2$ and heating with stirring. $Na_3C_6H_5O_7$ and $CH_3COONa$, as a complexing agent of $Ni^{2+}$, function by controlling the concentration of $Ni^{2+}$ in solution. The pH value adjusts the reduction rate of $Ni^{2+}$, and the formation rate of the Ni—P amorphous alloy. That is to say, the formation rate of Ni—P amorphous alloy is slow due to the pH value of 5.0. The existence of $Na_3C_6H_5O_7$ and $CH_3COONa$, is advantageous for depositing Ni—P amorphous alloy on the SiO, carrier. However, because the reduction of $Ni^{2+}$ is conducted in solution, only a small proportion of the Ni—P amorphous alloy is actually deposited onto, and supported by, the carrier itself. Most of the Ni—P amorphous alloy is left on the wall or the bottom of the container, so that the yield of the supported Ni—P amorphous alloy on the $SiO_2$ carriers is very low. Furthermore, Ni(Fe/Co)—B and Ni(Fe/Co)—P can itself function as a catalyst in $Ni^{2+}$ reduction (see Shen et al. J. Phys. Chem 97, 8504–8511, (1993)). Therefore, since the amount of Ni—P amorphous alloy not supported on the $SiO_2$ carrier exceeds that supported by $SiO_2$ carrier, the reduction and deposition rate of Ni—P amorphous alloy on the wall or at bottom of the container is in turn further enhanced, so that the proportion of Ni—P amorphous alloy supported on the SiO, carriers decreases still further.

(2) $Na_3C_6H_5O_7$ and $CH_3COONa$, as a complexing agent of $Ni^{2+}$ can control the reaction rate of $Ni^{2+}$, and is advantageous for supporting Ni—P amorphous alloy on the carrier. However, due to shielding of the complexing agent, the degree of reduction of $Ni^{2+}$ is lowered, so that a proportion of the $Ni^{2+}$ cannot be reduced by $H_2PO_2^-$. Thus, the cost for producing such a catalyst increases.

(3) The activity of the catalyst does not meet expected levels. Since the Ni(Fe/Co)—B and Ni(Fe/Co)—P can function as catalysts in $Ni^{2+}$ reduction, if the above-mentioned amorphous Ni—P alloy is pre-supported homogeneously throughout the carrier, $Ni^{2+}$ will be catalytically reduced inside the carrier by $H_2PO_2^-$. Thus, a majority of the Ni—P amorphous alloy will be uniformly absorbed onto the carrier with the assistance of induction and catalysis by Ni(Fe/

Co)—B and Ni(Fe/Co)—P. However, when a catalyst was prepared according to the process disclosed in Jingfa & Xiping, Appl. Catal. 37 339–343 (1988), the reduction is substantially conducted in solution. The Ni—P amorphous alloy consequently formed will be supported predominantly on the surface of the carrier. It is, therefore, difficult to obtain a product wherein the Ni—P amorphous alloy is uniformly deposited and supported throughout the carrier. In addition, there are no reports in the prior art of Ni—P amorphous alloy catalysts uniformly supported on a carrier.

According to Shen et al., J. Phys. Chem. 97, 8504–8511 (1993), the reaction between the metal ion $M^{2+}$ and the reducing agent $BH_4^-$ in an aqueous solution follows the three independent reactions given below:

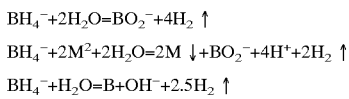

Since all three reactions proceed very rapidly, it could not be guaranteed that the resulting Ni—B amorphous alloy could be deposited efficiently on the carrier when the chemical plating is employed, when the carrier and the plating solution were mechanically mixed. Also, the homogeneous distribution of Ni—B amorphous alloy on the carrier could not be achieved. Therefore, there is a need to deposit and support Ni—B amorphous alloy uniformly on and throughout a carrier.

SUMMARY OF THE INVENTION

One object of the invention is to provide a new kind of supported amorphous alloy catalyst containing Ni and P, this catalyst comprising a porous carrier, a Ni—P amorphous alloy supported on the carrier, and a catalytic component which has been pre-supported on the carrier for the purpose of inducing and catalyzing the formation of the said Ni—P amorphous alloy onto the carrier. The pre-supported catalytic component according to a preferred embodiment of the present invention is Ni—B amorphous alloy.

The catalyst according to another preferred embodiment of the present invention further comprises a metal additive (M), and the said metal additive (M) refers to one or more metal elements, except Ni, which can be reduced, from their corresponding salts, into the elemental forms by the $H_2PO_2^-$ ion. In the inventive catalyst, the metal additive (M) may be present in the form of Ni—M—P amorphous alloy, or in the form of a mixture of Ni—P amorphous alloy with a polycrystalline metal additive (M).

Another object of the invention is to provide a process for the preparation of an amorphous alloy catalyst comprising pre-supporting the catalytic component onto the porous carrier, then supporting the Ni—P or Ni—M—P amorphous alloy, or the mixture of Ni—P amorphous alloy with the polycrystalline metal additive (M), onto the carrier.

According to a preferred embodiment of the present invention, Ni—B amorphous alloy as the catalytic component, is pre-supported onto the porous carrier; the Ni—P or Ni—M—P amorphous alloy or the mixture of Ni—P with the polycrystalline metal additive (M) is then deposited onto the carrier.

A further object of the invention is the use of such amorphous alloy catalysts in the hydrogenation of compounds having unsaturated functional groups.

DETAILED DESCRIPTION OF THE INVENTION

The invention provides an amorphous alloy catalyst comprising a porous carrier, a Ni—P amorphous alloy supported on the carrier, and a catalytic component which has been pre-supported onto the carrier for the purpose of inducing and catalyzing the formation of the Ni—P amorphous alloy onto the carrier.

The catalytic component in the catalyst according to the invention refers to any material which can be deposited homogeneously onto, and thereby supported by, the porous carrier, at such an amount that it can induce and catalyze the formation and deposition of the Ni—P or Ni—M—P amorphous alloy or the mixture of Ni—P amorphous alloy with the polycrystalline metal additive (M), onto the carrier. A preferred pre-supported catalytic component is an amorphous alloy of one or more metal(s) with boron. More preferably, an amorphous alloy of a metal is selected from group VIII, such as Ni, Fe, Co, Ru, Rh, Pd, Os, Ir, or Pt together with boron. A Ni—B amorphous alloy is most preferable.

The catalyst according to the invention preferably comprises, 0.15–30 wt % of Ni based on the total weight of the catalyst, 0.03–10 wt % of P based on the total weight of the catalyst, 0.01–10 wt % of pre-supported catalytic component (more preferably 0.01–5 wt %), based on the total weight of the catalyst, and a porous carrier.

The preferred catalyst according to the invention comprises a porous carrier, 0.15–30 wt % of Ni, based on the total weight of the catalyst, preferably 0.5–20 wt %, more preferably 1–15 wt %; 0.03–10 wt % of P, based on the total weight of the catalyst, preferably 0.1–5 wt %, more preferably 0.1–2.5 wt %; and 0.01–3.5 wt % of B, based on the total weight of the catalyst, preferably 0.02–2 wt %, more preferably 0.02–1 wt %. Ni is deposited onto the carrier in the form of Ni—P or Ni—B amorphous alloy. In the Ni—P amorphous alloy, the atomic ratio Ni/P is 0.5–10, preferably 1–5, and in the Ni—B amorphous alloy, the atomic ratio Ni/B is 0.5–10, preferably 0.5–5.

The catalyst according to the invention may further comprise 0.01–20 wt % of metal additive (M), based on the total weight of the catalyst. The metal additive (M) refers to one or more metal elements, except Ni, which can be obtained by reducing the corresponding salts with a solution containing hypophosphite ($H_2PO_2^-$). In the inventive catalyst, the metal additive (M) may be present in the form of an Ni—M—P amorphous alloy, or in the form of a mixture of Ni—P amorphous alloy with the polycrystalline metal additive (M). The content of the metal additive (M) is preferably 0.01–10 wt %, more preferably 0.01–5 wt %, based on the total weight of the catalyst.

In the preferred catalyst comprising a metal additive (M) according to the present invention, the atomic ratio (Ni+M)/P in Ni—M—P amorphous alloy, or in the polycrystalline phase of Ni—P amorphous alloy with the metal additive (M), is preferably in the range of 1–6. The atomic ratio Ni/M is preferably in the range of 1–700, and the atomic ratio Ni/B in the Ni—B amorphous alloy is preferably in the range of 1–5.

The porous carrier described in the present invention refers to the non-oxidizable porous carrier material. A preferred porous carrier is any one selected from porous inorganic oxide, active carbon, zeolite, molecular sieve or any mixtures thereof. The porous inorganic oxide refers to one or more solid oxides of those elements of group IIA, IIIA, IVA and IVB of the periodic system, among which one or more of the oxides from the group comprising $SiO_2$, $Al_2O_3$, $Zro_2$, $TiO_2$, MgO, and CaO are preferred. Zeolite and molecular sieve refer to various kinds of aluminosilicate zeolite, and molecular sieves containing heteroatoms, such as A-type zeolite, X-type zeolite, Y-type zeolite, ZSM zeolite series, mordenite, Beta zeolite, Ω-zeolite, P—Al molecular sieve, Ti—Si molecular sieve, etc. The preferred porous carrier is $SiO_2$, $Al_2O_3$ or active carbon.

The metal additive (M) in the present invention refers to one or more metal elements, except Ni, which can be obtained by reducing their corresponding salts by a solution containing $H_2PO_2^-$. The preferred metal additive (M) is selected from one or more metal elements in the groups IVA, IB, IIB, IIIB, VIB, VIIB and VIII, but excluding Ni. A more preferred metal additive (M) is selected from one or more metal elements in the groups IB, IIB, VIB. VIIB, and VIII, excluding Ni The most preferable metal additive (M) is selected from one or more metal elements in the group IB, VIB and VIII, such as Cu, Mo, W, Fe, and Co.

The specific surface area of the catalyst of the present invention could vary in range from 10 to 1000 $m^2/g$, preferably 100 to 1000 $m^2/g$, depending on the specific surface area of the carrier.

All of the Ni active component in the catalyst of the present invention may exist in an amorphous alloy state which may be confirmed by the X-ray diffraction (XRD) patterns with CuK α target. As shown in FIG. 1(1), a broad peak around 2θ=450 is observed. The shape of this broad peak may vary, depending on the carriers used. For example, when the carrier is active carbon, the peak is appreciably sharper, as shown in FIG. 1(2). In other cases, diffractional peaks of the carrier which locate at the same positions, may be superimposed on the broad peak as shown in FIG. 1(3). The metal additive (M) may also form an amorphous alloy in combination with Ni—P, as Ni—M—P, again confirmed by the X-ray diffraction (XRD) patterns with the CuK α target. As shown in FIG. 2(4), a broad peak around 2θ=45° is observed. The metal additive (M) may also be present in a polycrystalline phase formed with Ni—P amorphous alloy. This will give diffractional peaks, of the polycrystalline phase containing such a metal additive, observed from XRD patterns using a CuK α target, as shown in FIG. 2(5). In some cases diffractional peaks of the carrier may be superimposed on the broad peak around 2θ=45° from the Ni—M—P amorphous alloy, and/or the diffractional peaks derived from the polycrystalline phase containing the metal additive (M), as shown in FIGS. 3 and 4.

There may be one or more maximal temperature(s) at which phase transition takes place (FIG. 5). Also, depending upon the catalyst of the invention, the DSC curve may vary with the carrier (FIGS. 6 and 7).

The process for the preparation of the catalyst according to the present invention, using Ni—B amorphous alloy as the pre-supported catalytic component, is described in more detail as follows:

(1) Preparation of the porous carrier material pre-supported with Ni—B amorphous alloy: The porous carrier containing 0.1–20 wt % of Ni, based on the total weight of the catalyst, is contacted with a $BH_4^-$—containing solution at a concentration of 0.17–10 M, at a temperature between the melting point of the solution and 100° C., wherein the atomic ratio OF B/Ni is in the range of 0.1–10. The solid product is then washed with distilled water until it is free from acidic ions. The resulting porous carrier material contains 0.1–20 wt % of Ni—B amorphous alloy, based on the total weight of the catalyst, with the atomic ratio Ni/B in the range of 0.5–10.

(2) The porous carrier material pre-supported with Ni—B amorphous alloy is contacted with a mixed solution containing $H_2PO_2^-$ and $Ni^{2+}$ at a temperature between the melting point of the solution and 100° C. The concentration of $H_2PO_2^-$ in the mixed solution is of the range 0.01–5 M, and the concentration of $Ni^{2+}$ is of the range 0.01–5 M. The atomic ratio P/Ni is above 0.5. The solid product is washed until it is free from acidic ions, whereupon the inventive catalyst is obtained.

The porous carrier containing Ni can be obtained commercially, or by introducing Ni into a porous carrier, for example, by impregnating a porous carrier with a soluble Ni-salt solution by conventional methods. The impregnation with the Ni-salt solution can be conducted using those methods which are widely used in catalyst preparation, such as mechanical mixing. The said impregnation may also be replaced by other methods, such as blending and kneading. Ion exchange techniques could be employed to absorb Ni onto the carrier, when zeolites or molecular sieves, or other ion exchangeable carriers, are used as the porous carrier. Soluble Ni-salts may be selected from the group consisting of $NiCl_2$ $NiSO_4$, or one of the soluble nickel carboxylates. $NiCl_2$ and $NiAc_2$ are preferred. The Ni content in the Ni-containing porous carrier is in the preferred range of 0.8–8 wt %, based on the total weight of the catalyst. Preferably, the Ni-containing porous carrier has been pre-dried at 90–200° C. for at least three hours.

The most commonly used solution containing $BH_4^-$ ions refers to either of a $BH_4^-$ containing aqueous solution or alcoholic solution. The source of $BH_4^-$ ions is selected from $KBH_4$ or $NaBH_4$, or a mixture thereof.

The contact and reaction between porous carriers containing Ni, and the $BH_4^-$-containing solution, could be performed at a temperature higher than 100° C. However, temperature is usually maintained between the melting point and 100° C., most preferably between room temperature and 50° C. for energy economy. The contact time can vary with the reaction temperature. When the reaction temperature is higher, the reaction will be conducted more quickly and thus needs a shorter reaction time; when the reaction temperature is lower, the reaction period should be increased. Much $H_2$ will be released during the reaction. When no more $H_2$ is released, the reaction has reached completion. The contact time refers to the time from the beginning of the reaction to the point where no more $H_2$ is released.

The contact of a porous carrier containing Ni with a solution containing the $BH_4^-$ ion can be carried out by mixing them directly. Preferably the solution containing $BH_4^-$ is added dropwise to the porous carrier containing Ni.

With the porous carrier containing Ni—B amorphous alloy, the content of the Ni—B amorphous alloy is preferably in the range of 0.5–8 wt %, based on the total weight of the catalyst. The atomic ratio of Ni/B is preferably in the range of 1–5.

Preferably, the mixed solution containing $H_2PO_2^-$ and $Ni^{2+}$ ion is an aqueous solution. The precursor of the $H_2PO_2^-$ can be selected from $KH_2PO_2$ or $NaH_2PO_2$ with or without water of crystallization, or a mixture thereof. The precursor of $Ni^{2+}$ can be selected from soluble Ni salts, such as $NiCl_2$, $NiSO_4$, one or more of soluble nickel carboxylates; $NiCl_2$ and $NiAc_2$ are preferred. The atomic ratio P/Ni in the solution is preferably above 1, more preferably in the range of 3–7.

The weight ratio of porous carrier containing Ni—B amorphous alloy to $Ni^{2+}$ in the solution may be in the range of 1–1000, preferably 5–200, more preferably in the range of 5–100.

The mixed solution containing $H_2PO_2^-$ and $Ni^{2+}$ ion may further contain 0.01–3 M of metal additive (M) ion, the atomic ratio P/(Ni+M) is preferably above 0.5, more preferably above 1, most preferably in the range of 3–7.

The said metal additive (M) ion refers to one or more metal ions, except $Ni^{2+}$, which can be reduced into elemental states from their corresponding salts by a solution containing $H_2PO_2^-$. The preferred metal additive (M) ion is selected from one or more metal ions in the groups IVA, IB, IIB, IIIB, VIB, VIIB, and VIII, excluding $Ni^{2+}$, such as $Fe^{2+}$, $Co^{2+}$, $Cu^{2+}$, $MoO_4^{2-}$, $WO_4^{2-}$, or metatungstate ion. The more preferred metal ion is selected from one or more metal ions in the periodic groups IB, IIB, VIB, VIIB and VIII, excluding $Ni^{2+}$, such as $Fe^{2+}$, $Co^{2+}$, $Cu^{2+}$, $MoO_4^{2-}$, $WO_4^{2-}$ or metatungstate.

The contact and reaction between the porous carrier containing Ni—B amorphous alloy, and the mixed solution containing $H_2PO_2^-$ and $Ni^{2+}$ (and, if required, a metal additive (M) ion) could be performed at a temperature greater than 100° C. However, the temperature is usually controlled between the melting point and 100° C. for energy economy, preferably in the range of room temperature to 50° C. The contact time may vary with reaction temperature. When the reaction temperature is higher, the reaction will take place more quickly and thus the reaction needs a shorter time for completion; when the reaction temperature is reduced, the reaction needs a longer period to complete. Much $H_2$ will be generated when $H_2PO_2$ reduces $Ni^{2+}$ and/or the metal additive (M) ion, and the reaction would be deemed completed when no more $H_2$ is released. The contact time refers to the time from the beginning of the reaction, to the time point at which no more $H_2$ is released.

The contact and reaction of porous carrier containing Ni—B amorphous alloy with a mixed solution containing $H_2PO_2^-$ and $Ni^{2+}$ and, possibly a metal additive (M) ion, can be carried out in the following manner: mixing them directly and then followed by standing, or with stirring; or slowly adding dropwise the mixed solution containing $H_2PO_2^-$ and $Ni^{2+}$ to the porous carrier containing Ni—B amorphous alloy. Preferably, the contact and reaction is effected by directly mixing the porous carrier containing Ni—B amorphous alloy with the mixed solution containing $H_2PO_2^-$ and $Ni^{2+}$, followed by stirring.

The catalyst provided by the present invention can be employed in the hydrogenation of compounds containing unsaturated functional groups, and the said compounds may be alkenes, alkynes, aromatic hydrocarbons, nitrocompounds, keto-compounds, carboxyl compounds and nitrites. The hydrogenation refers to the saturated or selective hydrogenation, especially the selective hydrogenation of trace ethyne in ethylene. The hydrogenation conditions are those commonly used in such hydrogenation reactions.

The catalyst according to the present invention has the following advantages:

(I) The catalyst of the present invention exhibits superior hydrogenation activities over all prior art amorphous alloy catalysts reported so far. For example, the catalytic activities of the following catalysts were evaluated by the selective hydrogenation of trace ethyne in ethylene at T=110° C., P=10.0 MPa, and the space velocity (gas volume)=9000 hour$^{-1}$: (1) the inventive Ni—P amorphous alloy catalyst with 3.98 wt % of Ni, based on the total weight of the catalyst, wherein Ni—B amorphous alloy was used as the catalytic component pre-supported onto $SiO_2$; (2) the Ni—La—P amorphous alloy catalyst with high specific surface area reported in CN 1073726A; (3) supported Ni—P/$SiO_2$ catalyst with 11.70 wt % of Ni, based on the total weight of the catalyst, disclosed by Jingfa & Xiping, App. Catal. 37, 339–343 (1988); and (4) the traditional polycrystalline Ni catalyst with 5 wt % of Ni, based on the total weight of the catalyst. The conversion of ethyne by each catalyst is shown in FIG. 9 (plots 6, 9, 10, and 11 respectively).

The catalytic activities of the following catalysts were also evaluated by the selective hydrogenation of trace ethyne in ethylene at T=110° C., P=10.0 MPa, and the space velocity (gas volume)=9000 hour$^{-1}$: (1) the inventive amorphous alloy catalyst with 6.61 wt % of Ni, based on the total weight of the catalyst, 0.09 wt % of Co, based on the total weight of the catalyst, 0.09 wt % of P, based on the total weight of the catalyst, and 0.03 wt % of B, based on the total weight of the catalyst, supported onto $SiO_2$; (2) the inventive amorphous alloy catalyst with 6.54 wt % of Ni, based on the total weight of the catalyst, 0.35 wt % of Fe, based on the total weight of the catalyst, 1.08 wt % of P, based on the total weight of the catalyst, 0.03 wt % of B, based on the total weight of the catalyst, supported onto $SiO_2$; (3) the Ni—La—P amorphous alloy catalyst with 87.4 wt % of Ni, based on the total weight of the catalyst, and high specific surface area as reported in CN 1073726A; (4) the supported Ni—P/$SiO_2$ catalyst with 11.70 wt % of Ni, based on the total weight of the catalyst, disclosed by Jingfa & Xiping (Appl. Catal. 37, 339–343, (1988)). The conversion of ethyne by each catalyst is shown in FIG. 10 (plots 12, 13, 15, 16, respectively).

These results demonstrate that the reactivity of the catalysts according to the present invention is much superior over those known from prior art techniques, including the most active amorphous alloy catalyst with high specific surface area known from the prior art. On the other hand, the inventive catalysts described above have a much lower Ni content (3.98, 6.61 and 6.54 wt % of Ni, based on the total weight of the catalyst, respectively) than the Ni—La— P amorphous alloy catalyst with high specific surface area (87.4 wt % of Ni). The inventive catalyst is thus a catalyst having low Ni content and high activity.

(II) The specific surface area of the catalyst of the present invention could be adjusted freely by choosing carriers with different specific surface areas as required. The specific surface area may be varied between 10 to 1000 m$^2$/g, preferably between 100 and 1000 m$^2$/g. In contrast, the specific surface area of the ultra-fine Ni—B and Ni—P amorphous alloy catalyst disclosed by Dichang et al., J. Catal. 150, 434–438 (1994), are 29.7 m$^2$/g and 2.78 m$^2$/g, respectively. The specific surface area of the Ni—P/$SiO_2$ amorphous alloy reported by Jingfa & Xiping, App. Catal. 37, 339–343 (1988) is 85 m$^2$/g. The specific surface area of Ni—RE—P amorphous alloy catalysts is at most 130 m$^2$/g which is the highest known from the prior art.

(III) The catalyst of the present invention exhibits excellent thermal stability. Its maximal crystallization temperature is 434° C., which is 81° C. higher than the highest crystallization peak temperature of the Ni—P—$SiO_2$ amorphous alloy catalysts reported by Jingfa & Xiping, App. Catal. 37, 339–343 (1988), and is 164° C. higher than the highest crystallization temperature of the Ni—La—P amorphous alloy with high specific surface area.

According to the process for the preparation of the inventive catalyst, the absorption of Ni—B amorphous alloy onto the porous carrier is conducted first. The porous carrier pre-supported with Ni—B amorphous alloy is then contacted with a mixed solution containing $H_2PO_2^-$ and $Ni^{2+}$, and any metal additive (M) ion, if required, so as to effect the formation of the Ni—P or Ni—M—P amorphous alloy by reduction. The pre-supported Ni—B functions as the catalytic component, and catalyzes the reduction of $Ni^{2+}$ and/or metal additive (M) ion by $H_2PO_2^-$ inside the carrier. This ensures that almost all of the Ni—P amorphous alloy or Ni—M—P amorphous alloy, or the mixture of Ni—P amorphous alloy with the polycrystalline additive metal (M) formed, could be supported by the interstitial and inner surfaces of the pores of the porous carrier. The resulting amorphous alloy in turn becomes the catalyst of the reduction, and further accelerates the formation of the amorphous alloy within the carrier. As a result, almost all of the Ni—P amorphous alloy or Ni—M—P amorphous alloy, or the mixture of Ni—P amorphous alloy with the polycrystalline additive metal (M) will be homogeneously supported on the interstitial and inner surface and/or inside the pores of the porous carrier. In contrast, in the process disclosed by Jingfa & Xiping, App. Catal. 37, 339–343 (1988), only 20.1 wt %, based on the total weight of the catalyst, of Ni—P amorphous alloy could be supported on the surface of porous carrier, with the majority being left on the wall or at the bottom of the container. Thus, the process for the preparation of the catalyst according to the invention substantially enhances the efficiency of deposition of Ni on the carrier, which ranges from 21.3–98.4 wt %, based on the total weight of the catalyst, in contrast to 16.9 wt %, according to the process of Jingfa & Xiping.

EXAMPLES

Figure 1:
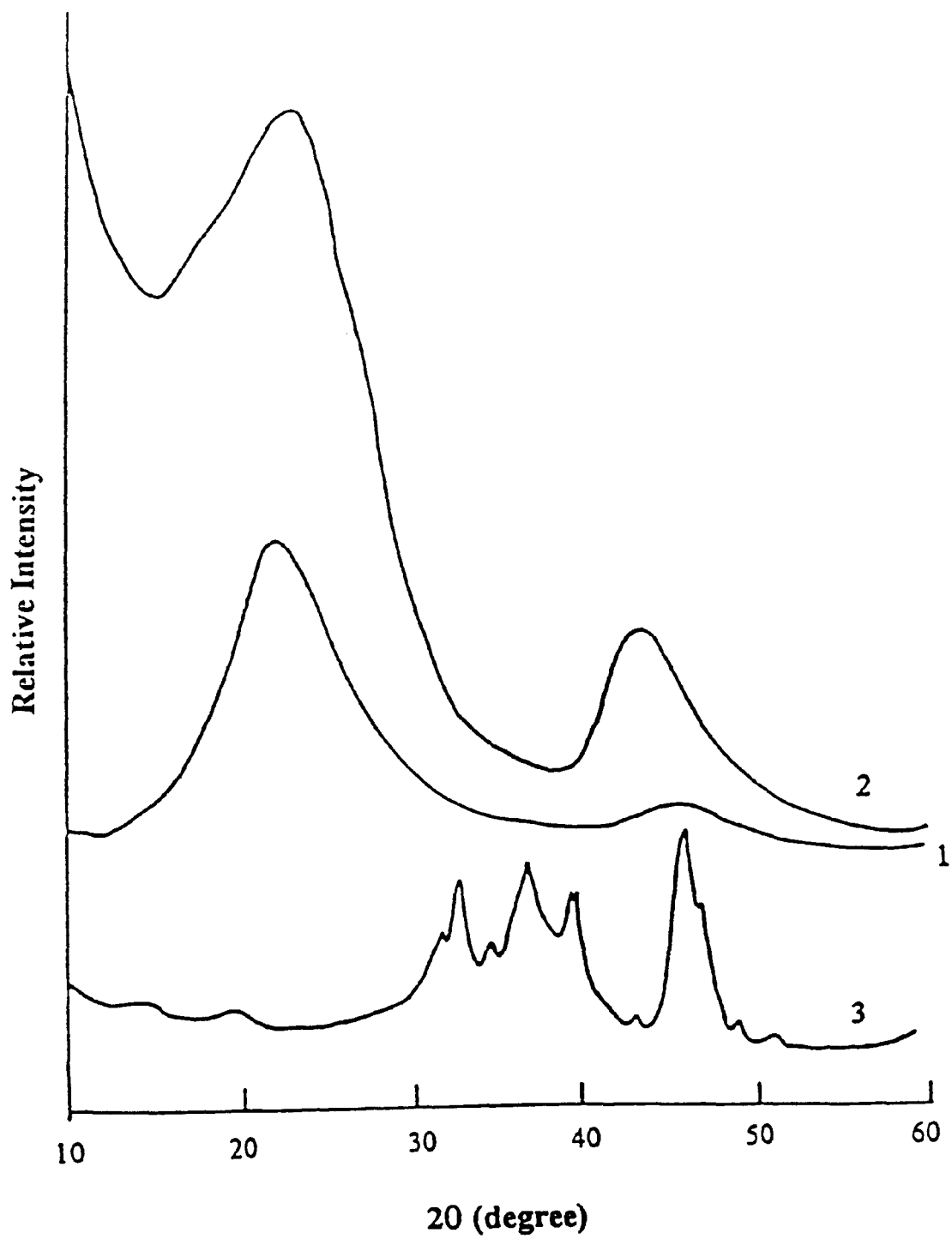
FIG. 1 shows the XRD patterns of the catalysts containing Ni—P amorphous alloy using various carriers according to the present invention.

The following examples are given only for the purpose of a detailed explanation of the present invention. It should be stressed that the present invention is not limited by these examples.

Examples 1–15

The following examples describe the catalyst and the process for preparation according to the invention.

(1) Carriers

The carrier I (No. $Z_1$) refers to the silica gel with big pore size which is available from Qingdao Haiyang Chemical and Engineering Company, China; carrier 2 (No. $Z_2$) refers to the silica gel with small pore size which is available from the same company; carrier 3 (No. $Z_3$) refers to active carbon which is available from Beijing Guanghua Wood Factory, China; carrier 4 (No. $Z_4$) refers to the __-$Al_2O_3$ which is prepared by calcining a spherical $Al_2O_3$ at 900° C. for 4 hours, which is used as the carrier of CB-8 catalyst and is available from Changling Catalyst Company, China; carrier 5 (No. $Z_5$) refers to the __-$Al_2O_3$ which is prepared by calcining a spherical $Al_2O_3$ at 650° C. for 4 hours, which is also used as the carrier of CB-8 catalyst and is available from Changling Catalyst Company, China. Carriers $Z_1$–$Z_5$; are in granular form with a particle size of 80–120 mesh. The physiochemical properties of these carriers ($Z_1$–$Z_5$) are summarized in Table 1, in which the crystalline phases are determined by XRD, and the specific surface area and pore volume are determined by BET nitrogen adsorption at low temperature.

TABLE I

| Carrier No. | Type of Carrier | $S_{BET}$, $M^2$/g | $V_{pore}$, ml/g | Cryst. Phase |
|---|---|---|---|---|
| $Z_1$ | $SiO_2$ | 401 | 0.95 | Amorphous |
| $Z_2$ | $SiO_2$ | 672 | 0.39 | Amorphous |
| $Z_3$ | Active carbon | 888 | 0.56 | Amorphous |
| $Z_4$ | $Al_2O_3$ | 124 | 0.49 | $\delta$ |
| $Z_5$ | $Al_2O_3$ | 153 | 0.47 | $\gamma$ |

(2) Preparation of the porous carrier pre-supported with Ni—B amorphous alloy

Quantities of each carrier mentioned above ($Z_1$–$Z_5$) are dried at 100–150° C. Nickel acetate ($Ni(CH_3COO)_2$) is dissolved in distilled water to prepare aqueous solutions, and the above carriers are immersed therein. The Ni-impregnated carriers are dried at 120° C. Aqueous solutions of $KBH_4$ are then added dropwise to the individual Ni-impregnated carriers at room temperature. The reduction reaction is initiated immediately with the generation of $H_2$. After completion of the reaction, indicated by cessation of $H_2$ release, the resulting solid products are washed with distilled water until free from acidic ions, giving a porous carrier pre-supported with Ni—B amorphous alloy ($S_1$–$S_7$) (Table 3). The amounts of various materials used are shown in Table 2. The specific surface areas of, and contents of Ni—B in the porous amorphous alloy, in $S_1$–$S_7$ are given in Table 3. The contents of Ni and B are determined by ICP on a Jarrel-Ash 1000 after the sample is dissolved by a microwave method. The measurement of specific surface area and pore volume are performed by the same method mentioned above.

TABLE 2

| Carrier | | NiAc$_2$ solution | | KBH$_4$ solution | | Ni—B/ |
|---|---|---|---|---|---|---|
| Type | W (g) | $W_{NiAc2-4H2O}$ (g) | $W_{H2O}$ (g) | $W_{JBH4}$ (g) | $W_{H2O}$ (g) | Carrier |
| $Z_1$ | 5.0 | 0.2 | 9.0 | 0.11 | 12.0 | $S_1$ |
| $Z_1$ | 5.0 | 0.5 | 9.0 | 0.27 | 12.0 | $S_2$ |
| $Z_2$ | 5.0 | 0.2 | 9.0 | 0.11 | 12.0 | $S_3$ |
| $Z_3$ | 5.0 | 0.5 | 9.0 | 0.27 | 12.0 | $S_4$ |
| $Z_4$ | 5.0 | 0.2 | 9.0 | 0.11 | 12.0 | $S_5$ |

TABLE 2-continued

| Carrier | | NiAc₂ solution | | | | |
|---|---|---|---|---|---|---|
| Type | W (g) | $W_{NiAc2-4H2O}$ (g) | $W_{H2O}$ (g) | $W_{JBH4}$ (g) | KBH₄ solution $W_{H2O}$ (g) | Ni—B/ Carrier |
| $Z_4$ | 5.0 | 1.0 | 5.0 | 0.54 | 7.0 | $S_6$ |
| $Z_5$ | 5.0 | 0.2 | 5.0 | 0.11 | 7.0 | $S_7$ |

TABLE 3

| Ni—B/ Carrier | Content of Ni—B (wt %) | Ni/B Atomic Ratio | Specific Surface Area m²/g |
|---|---|---|---|
| $S_1$ | 0.59 | 3.44 | 396 |
| $S_2$ | 1.57 | 4.63 | 385 |
| $S_3$ | 0.55 | 1.84 | 652 |
| $S_4$ | 1.56 | 3.41 | 868 |
| $S_5$ | 0.65 | 3.81 | 125 |
| $S_6$ | 3.96 | 1.27 | 129 |
| $S_7$ | 0.67 | 3.93 | 155 |

(3) Catalyst preparation

Nickel acetate (Ni(CH₃COO)₂) and sodium hypophosphite (NaH₂PO₂), are dissolved in distilled water. Then, samples of the carriers ($S_1$–$S_6$) are added into the aqueous solution of nickel acetate and sodium hypophosphite, under stirring. The reduction reactions are initiated immediately with the generation of H₂. After completion of the reaction, indicated by the cessation of H₂ release, the solid products are washed with distilled water till free from acidic ions, resulting in the catalysts of the present invention. They are numbered from $C_1$ to $C_{15}$ (Examples 1–15) respectively. The amounts of various materials used for the preparation, and reaction conditions, are shown in Table 4. The yields of Ni—P amorphous alloy and of Ni supported onto the carriers are given in Table 5, the compositions and properties of catalysts $C_1$–$C_{15}$ are given in Table 6. The XRD patterns of the catalysts $C_1$–$C_{12}$ are shown in FIG. 1(1), the XRD patterns of the catalyst $C_{13}$ is shown in FIG. 1(2), and the XRD patterns of the catalysts $C_{14}$ and $C_{15}$ are shown in FIG. 1(3).

The yields of Ni—P amorphous alloy and of Ni deposited onto the carriers refer to weight percentages of Ni—P amorphous alloy supported onto the carrier, based on the total weight of the Ni—P amorphous alloy formed (including Ni—P amorphous alloy unsupported on the carriers). The carrier used has a particle size of 80–120 mesh, while the unsupported portion of the formed Ni—P amorphous alloy is an extremely fine powder (>200 mesh). After sifting, the content of Ni—P amorphous alloy in the particle above and below 120 mesh is measured, and the yields are determined from following equations:

Yield of Ni—P amorphous alloy supported onto carrier =

(total amount of Ni and P supported onto carrier below 120 mesh – amount of Ni pre-supported onto carrier) /

(total amount of Ni—P formed by the reduction reaction) × 100%

Yield of Ni = (total amount of Ni supported onto the carrier – amount of Ni pre-supported onto carrier) /

(total amount of Ni added into the solution) × 100%

The contents of B, Ni and P are determined by ICP on a Jarrel-Ash 1000 after the sample is dissolved by a microwave method. The XRD is performed with a DIMAX-3A X-ray diffraction meter with CuK_as target, 40 kV tube voltage, 35 mA tube electric current. The measurement of the specific surface area of the catalysts are performed in the same method as mentioned above.

TABLE 4

| Exp. No. | Carrier containing Ni—B amorphous alloy | | Concentration of mixed solution, M | | Amount of Solution | Atomic Ratio | Reaction Temperature | Reaction Time |
|---|---|---|---|---|---|---|---|---|
| | Type | W (g) | Ni²⁺ | H₂PO₂ | ml | P/Ni | ° C. | Hour |
| 1 | $S_1$ | 5.00 | 0.10 | 0.10 | 40.00 | 1.00 | 25 | 3 |
| 2 | $S_1$ | 5.00 | 0.10 | 0.20 | 40.00 | 2.00 | 25 | 3 |
| 3 | $S_1$ | 5.00 | 0.10 | 0.30 | 40.00 | 3.00 | 25 | 3 |
| 4 | $S_1$ | 5.00 | 0.10 | 0.40 | 40.00 | 4.00 | 25 | 3 |
| 5 | $S_1$ | 5.00 | 0.10 | 0.50 | 40.00 | 5.00 | 25 | 3 |
| 6 | $S_1$ | 5.00 | 0.10 | 0.60 | 40.00 | 6.00 | 25 | 3 |
| 7 | $S_1$ | 5.00 | 0.10 | 0.70 | 40.00 | 7.00 | 25 | 3 |
| 8 | $S_2$ | 5.00 | 0.05 | 0.25 | 40.00 | 5.00 | 8 | 10 |
| 9 | $S_2$ | 5.00 | 0.05 | 0.30 | 40.00 | 6.00 | 25 | 2 |
| 10 | $S_2$ | 5.00 | 0.05 | 0.35 | 40.00 | 7.00 | 50 | 1.5 |
| 11 | $S_2$ | 5.00 | 0.05 | 0.40 | 40.00 | 8.00 | 90 | 1 |
| 12 | $S_3$ | 5.00 | 0.10 | 0.40 | 40.00 | 4.00 | 25 | 3 |
| 13 | $S_4$ | 5.00 | 0.12 | 0.48 | 40.00 | 4.00 | 25 | 2 |
| 14 | $S_5$ | 5.00 | 0.14 | 0.56 | 40.00 | 4.00 | 25 | 3 |
| 15 | $S_6$ | 5.00 | 0.22 | 0.88 | 40.00 | 4.00 | 25 | 1.5 |

TABLE 5

| Exp No. | Yield of Ni—P, wt % | Yield of Ni, Wt % |
|---|---|---|
| 1 | 100 | 21.3 |
| 2 | 100 | 36.0 |
| 3 | 100 | 56.2 |
| 4 | 100 | 76.0 |
| 5 | 100 | 75.8 |
| 6 | 100 | 81.4 |

TABLE 5-continued

| Exp No. | Yield of Ni—P, wt % | Yield of Ni, Wt % |
|---|---|---|
| 7 | 100 | 86.7 |
| 8 | 100 | 51.2 |
| 9 | 100 | 66.0 |
| 10 | 100 | 67.7 |
| 11 | 100 | 73.9 |
| 12 | 100 | 50.0 |
| 13 | 100 | 93.6 |
| 14 | 100 | 90.9 |
| 15 | 100 | 98.4 |

TABLE 6

| | | Composition of catalyst, wt % | | | | |
|---|---|---|---|---|---|---|
| Exp. No. | Catal. No. | Ni | Ni in Ni—P form | P | B | Atomic ratio Ni/P in Ni—P alloy | Surface Area ($m^2/g$) |
| 1 | $C_1$ | 1.55 | 0.99 | 0.11 | 0.03 | 4.75 | 384 |
| 2 | $C_2$ | 2.23 | 1.67 | 0.27 | 0.03 | 3.26 | 374 |
| 3 | $C_3$ | 3.12 | 2.56 | 0.46 | 0.03 | 2.94 | 364 |
| 4 | $C_4$ | 3.99 | 3.43 | 0.52 | 0.03 | 3.48 | 341 |
| 5 | $C_5$ | 3.98 | 3.42 | 0.52 | 0.03 | 3.47 | 341 |
| 6 | $C_6$ | 4.22 | 3.66 | 0.55 | 0.03 | 3.51 | 338 |
| 7 | $C_7$ | 4.45 | 3.89 | 0.62 | 0.03 | 3.31 | 330 |
| 8 | $C_8$ | 2.71 | 1.20 | 0.27 | 0.06 | 2.34 | 366 |
| 9 | $C_9$ | 3.03 | 1.52 | 0.33 | 0.06 | 2.43 | 367 |
| 10 | $C_{10}$ | 3.07 | 1.56 | 0.36 | 0.06 | 2.29 | 366 |
| 11 | $C_{11}$ | 3.21 | 1.70 | 0.37 | 0.06 | 2.42 | 365 |
| 12 | $C_{12}$ | 2.79 | 2.29 | 0.27 | 0.05 | 4.47 | 446 |
| 13 | $C_{13}$ | 6.46 | 4.98 | 0.63 | 0.08 | 4.17 | 786 |
| 14 | $C_{14}$ | 6.16 | 5.54 | 1.79 | 0.03 | 1.63 | 135 |
| 15 | $C_{15}$ | 12.96 | 9.50 | 2.71 | 0.50 | 1.84 | 136 |

Examples 16–26

The following examples describe the catalysts and their preparation according to the invention.

Figure 2:
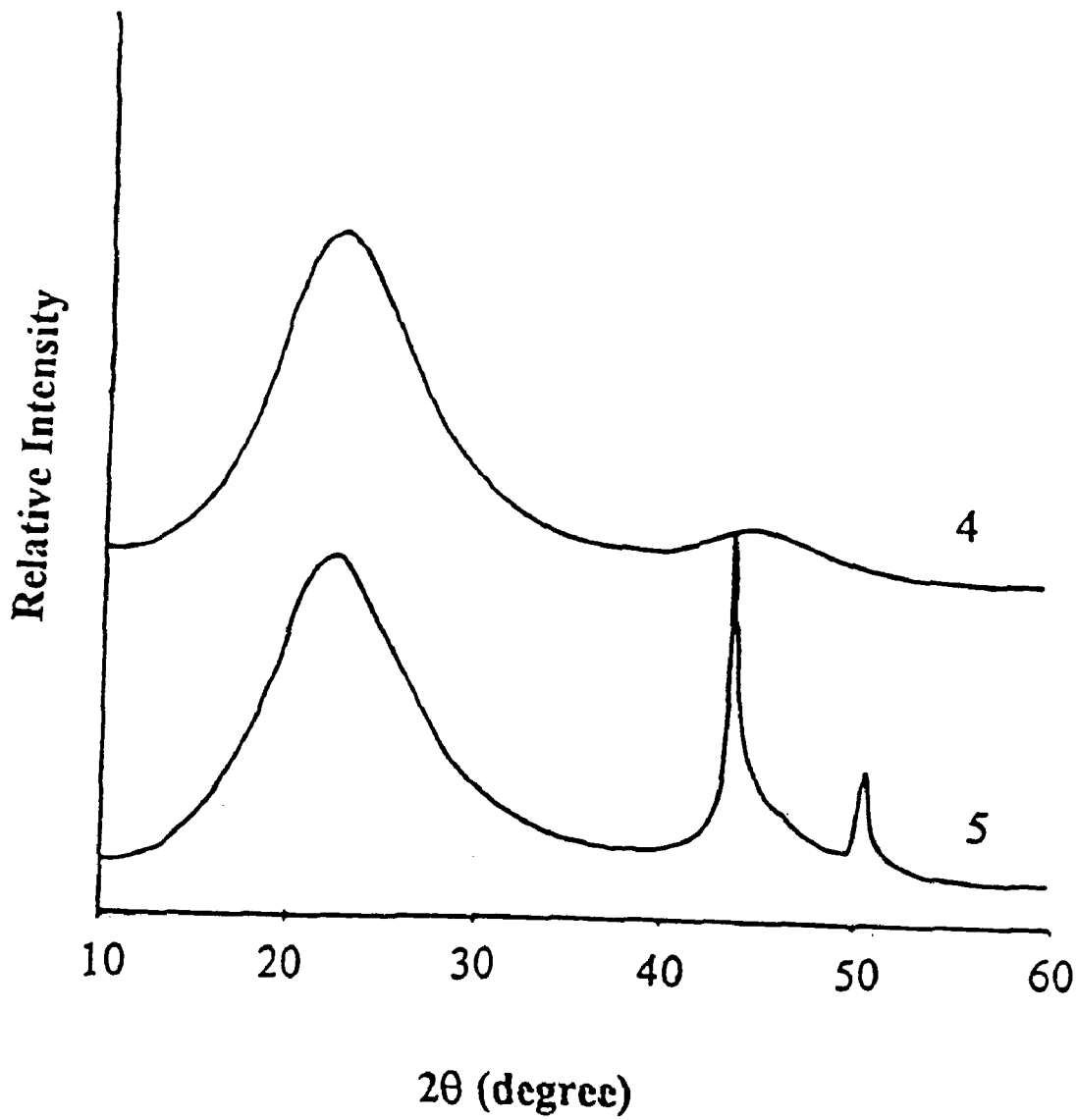
FIG. 2 shows the XRD patterns of the amorphous alloy catalysts containing a metal additive using $SiO_2$ as the carrier according to the present invention.
Figure 3:
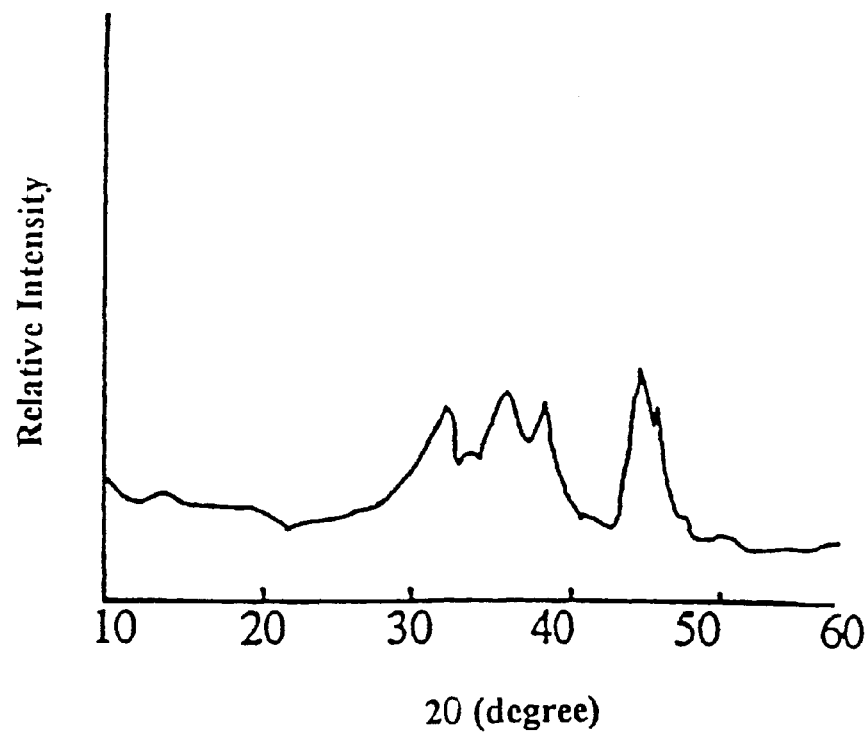
FIG. 3 shows the XRD patterns of the amorphous alloy catalysts containing a metal additive using $\delta$-$Al_2O_3$ as the carrier according to the present invention.
Figure 4:
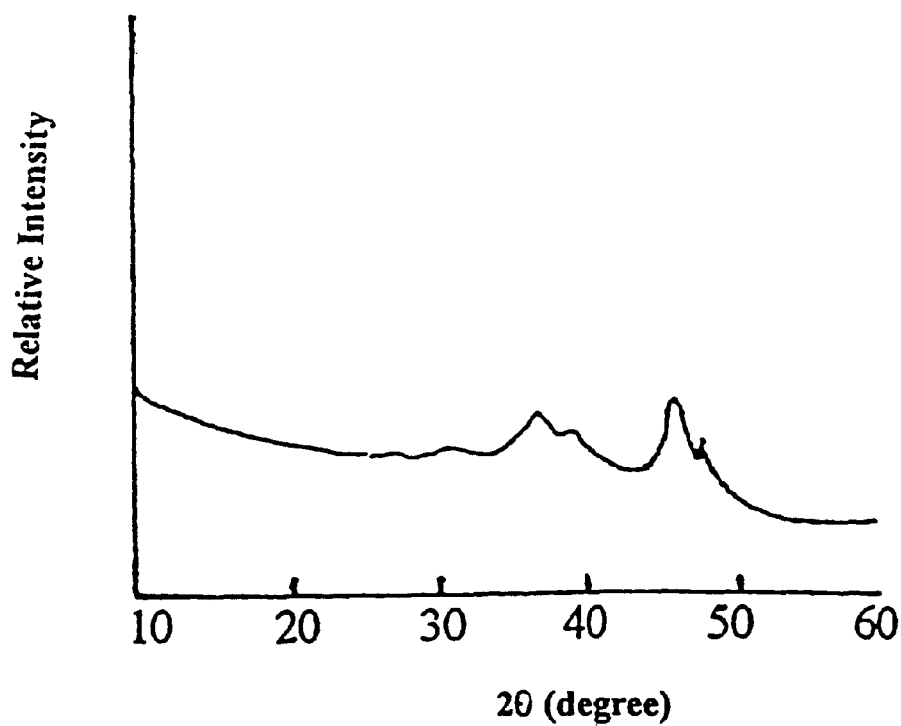
FIG. 4 shows the XRD patterns of the amorphous alloy catalysts containing a metal additive using $\gamma$-$Al_2O_3$ as the carrier according to the present invention.

Nickel acetate ($Ni(CH_3COO)_2$), sodium hypophosphite ($NaH_2PO_2$.), and salts containing metal additives (M), are dissolved in distilled water to obtain aqueous solutions. The carriers $S_1$, $S_3$, $S_5$–$S_7$, containing Ni—B amorphous alloy, are added into the aqueous solutions with agitation, at various temperatures. The reduction reaction is initiated immediately with the generation of $H_2$. After completion of the reaction indicated by cessation of $H_2$ release, the obtained solid products are washed with distilled water till free from acidic ions, resulting in the catalysts of the present invention. They are numbered as $C_{16}$ to $C_{26}$ (Examples 16–26). The amounts of various materials used in the preparation and reaction conditions are shown in Tables 7 and 8. The yields (denoted as $Y_I$) of the Ni—M—P amorphous alloy or the mixture of Ni—P amorphous alloy with the polycrystalline metal additives (M), and the yield of Ni (denoted as $Y_2$) supported onto the carriers are given in Table 9. The compositions and properties of catalysts $C_{16}$–$C_{26}$ are given in Table 10. The XRD patterns of the catalysts $C_{16}$–$C_{19}$, $C_{21}$, $C_{25}$, and $C_{26}$ are shown in FIG. 2(4), the XRD pattern of the catalyst $C_{20}$ is shown in FIG. 2(5), the XRD pattern of the catalysts $C_{22}$ and $C_{24}$ is shown in FIG. 3. The XRD pattern of the catalyst $C_{23}$ is shown in FIG. 4.

The yields ($Y_1$) of Ni—M—P amorphous alloy or polycrystalline phases of Ni—P amorphous alloy with metal additives (M) supported onto the carriers, refer to weight percentages of Ni—M—P amorphous alloy or the mixture of Ni—P amorphous alloy with the polycrystalline metal additives (M) supported onto the carriers, based on the total weight of Ni—M—P amorphous alloy formed by the reduction reaction (including Ni—M—P amorphous alloy unsupported onto the carriers). The carriers used have a particle size of 80–120 mesh, while the amorphous alloy or polycrystalline metal additive (M) formed is in the form of extremely fine powder (>200 mesh). After sifting, the content of Ni, M and P in the particle above and below 120 mesh are measured, and then the yields are determined from following equations:

$Y_1 =$ (total amount of Ni, P and M supported onto the carrier below 120 mesh − amount of Ni pre-supported onto carrier) / (total amount of Ni, P and M formed) × 100%

$Y_2 =$ (total amount of Ni supported onto carrier − amount of Ni pre-supported onto carrier) / (total amount of Ni added in the solution) × 100%

The contents of B, Ni, metal additive (M) and P are determined by ICP on a Jarrel-Ash 1000 after the sample is dissolved by a microwave method. The XRD and measurements of the specific surface area of the catalysts are performed in the same manner as mentioned above.

TABLE 7

| | Carrier | | mixed solution | | | | atomic | | weight | reaction | |
|---|---|---|---|---|---|---|---|---|---|---|---|
| Exp. No | Type | W (g) | $C_{NiAC2}$ (M) | M Salt[a] | $C_{SALT}$ (M) | $C_{NAH2PO2}$ (M) | $V^{b)}$ (ml) | ratio P/(Ni + M) | atomic ratio Ni/M | ratio of carrier/Ni | temp. ° C. | reaction time (hr) |
| 16 | $S_1$ | 5.0 | 0.15 | $NaMoO_4.2H_2O$ | 0.04 | 1.05 | 40.00 | 5.53 | 3.75 | 14.2 | 25 | 3.0 |
| 17 | $S_1$ | 5.0 | 0.15 | $NaWO_4.2H_2O$ | 0.04 | 1.05 | 40.00 | 5.53 | 3.75 | 14.2 | 50 | 2.5 |
| 18 | $S_1$ | 5.0 | 0.15 | $Co(CH_3COO)_2.4H_2O$ | 0.04 | 0.75 | 40.00 | 3.95 | 3.75 | 14.2 | 90 | 1.0 |
| 19 | $S_1$ | 5.0 | 0.15 | $FeSO_4.7H_2O$ | 0.04 | 0.75 | 40.00 | 3.95 | 3.75 | 14.2 | 8 | 10.0 |
| 20 | $S_1$ | 5.0 | 0.15 | $CuSO_4.5H_2O$ | 0.06 | 0.75 | 40.00 | 3.95 | 3.75 | 14.2 | 25 | 3.0 | note:
[a]The salt of metal additive (M);
[b]Volume of the mixed solution.

TABLE 8

| Exp. No | Carrier Type | W (g) | $C_{NiAC2}$ (M) | mixed solution M Salt[a] | $C_{SALT}$ (M) | $C_{NAH2PO2}$ (M) | $V^{b)}$ (ml) | atomic ratio P/(Ni + M) | atomic ratio Ni/M | weight ratio of carrier/Ni | reaction temp. ° C. | reaction time hour |
|---|---|---|---|---|---|---|---|---|---|---|---|---|
| 21 | $S_3$ | 5.0 | 0.15 | $FeSO_4.7H_2O$ | 0.04 | 0.75 | 40.00 | 3.95 | 3.75 | 14.2 | 25 | 3.0 |
| 22 | $S_5$ | 5.0 | 0.15 | $FeSO_4.7H_2O$ | 0.04 | 0.75 | 40.00 | 3.95 | 3.75 | 14.2 | 25 | 3.0 |
| 23 | $S_7$ | 5.0 | 0.15 | $FeSO_4.7H_2O$ | 0.04 | 0.75 | 40.00 | 3.95 | 3.75 | 14.2 | 25 | 3.0 |
| 24 | $S_6$ | 5.0 | 0.30 | $CuSO_4.5H_2O$ | 0.04 | 1.34 | 40.00 | 3.95 | 3.75 | 28.4 | 25 | 1.5 |
| 25 | $S_1$ | 5.0 | 0.02 | $Na_2MoO_4.2H_2O$ | 0.01 | 0.20 | 40.00 | 6.67 | 2.00 | 106.5 | 25 | 3.0 |
| 26 | $S_1$ | 5.0 | 0.45 | $Na_2MoO_4.2H_2O$ | 0.03 | 3.20 | 40.00 | 6.67 | 15.00 | 4.73 | 25 | 3.0 |

[a], [b] same as that in table 7.

TABLE 9

| Exp. No. | $Y_1$, wt % | $Y_2$, wt % |
|---|---|---|
| 16 | 100 | 92.1 |
| 17 | 100 | 93.0 |
| 18 | 100 | 92.4 |
| 19 | 100 | 91.7 |
| 20 | 100 | 97.3 |
| 21 | 100 | 91.7 |
| 22 | 100 | 91.7 |
| 23 | 100 | 91.0 |
| 24 | 100 | 88.4 |
| 25 | 100 | 79.5 |
| 26 | 100 | 69.3 |

TABLE 10

| Exp. No. | Catal. No. | Composition of catalyst, wt % Ni | Ni in Ni—M-P or in Ni—P | Metal additive M | P | B | Surface Area $(m^2/g)$ | Atomic ratio Ni/M | Atomic ratio (Ni + M)/P |
|---|---|---|---|---|---|---|---|---|---|
| 16 | $C_{16}$ | 6.59 | 6.03 | Mo 0.04 | 0.96 | 0.03 | 384 | 246 | 3.3 |
| 17 | $C_{17}$ | 6.65 | 6.09 | W 0.03 | 0.95 | 0.03 | 374 | 636 | 3.4 |
| 18 | $C_{17}$ | 6.61 | 6.05 | Co 0.09 | 0.90 | 0.03 | 364 | 67 | 3.6 |
| 19 | $C_{19}$ | 6.54 | 5.98 | Fe 0.35 | 1.08 | 0.03 | 341 | 16 | 3.1 |
| 20 | $C_{20}$ | 6.80 | 6.24 | Cu 2.88 | 0.88 | 0.03 | 341 | 2 | 5.3 |
| 21 | $C_{21}$ | 6.49 | 5.99 | Fe 0.34 | 0.98 | 0.05 | 338 | 17 | 3.4 |
| 22 | $C_{22}$ | 6.60 | 5.98 | Fe 0.34 | 1.01 | 0.03 | 130 | 17 | 3.3 |
| 23 | $C_{23}$ | 6.58 | 5.94 | Fe 0.36 | 1.03 | 0.06 | 162 | 16 | 3.2 |
| 24 | $C_{24}$ | 14.14 | 10.68 | Cu 1.91 | 1.66 | 0.05 | 145 | 6 | 4.0 |
| 25 | $C_{25}$ | 1.30 | 0.74 | Mo 0.01 | 0.19 | 0.03 | 398 | 121 | 2.1 |
| 26 | $C_{26}$ | 13.34 | 12.78 | Mo 0.04 | 1.45 | 0.03 | 385 | 522 | 4.7 |

It is known from the data in Tables 4–10 and FIG. 2 that:

(1) In the preparation of the catalysts according to the invention, all of the Ni—P amorphous alloy, N—M—P amorphous alloy and polycrystalline phase of Ni—P amorphous alloy with metal additives, are supported onto carrier. According to the process disclosed in Appl. Catal. 37, 339–340, (1988), most of the amorphous alloy formed is not supported onto the $SiO_2$ carrier, the yield of Ni—P amorphous alloy supported onto $SiO_2$ carrier is only 20.1 wt %, based on the total weight of the catalyst. The inventive process, therefore, is superior to the process disclosed by the prior art.

(2) According to the process of the invention, the yield of Ni ranges from 21.3–98.4 wt %, based on the total weight of the catalyst, and is obviously higher than that obtained by the process disclosed in Appl. Catal. 37, 339340, (1988), in which it is only 16.9 wt %. The inventive process is, therefore, superior to the process disclosed by the prior art.

(3) When metal additive (M) is used for the preparation of the inventive catalyst, metal additive (M) may be present in the form of Ni—M—P amorphous alloy, which is confirmed by the X-ray diffraction (XRD) patterns with CuK __ as target. A broad peak around $2\theta=45°$ is observed (if $SiO_2$ is used as carrier, and Mo, W, Co and Fe as the metal additive). It may also be present in the form of a polycrystalline phase of Ni—P amorphous alloy with metal additive (M), which is confirmed by the X-ray diffraction (XRD) patterns with CuK__ as target. A peak of polycrystalline phase of metal additive (M) is observed (if $SiO_2$ is used as carrier, and Cu as metal additive, a peak of polycrystalline phase is observed around $2\theta=43°$ and $51°$). In some cases, the broad peak, or the peak of the mixture of amorphous alloy with the polycrystalline metal additive may be covered by the diffractional peaks at the same positions originating from the carrier, (if __-$Al_2O_3$ or __-$Al_2O_3$ is used).

Comparative Example 1

Preparation of comparative Ni—P/$SiO_2$ amorphous alloy catalyst.

According to the process disclosed by Jingfa & Xiping, Appl. Catal. 37, 339–340, (1988), 40 ml of a solution containing sodium citrate ($Na_3C_6H_5O_7.H_2O$) (10 g/l), nickel sulfate ($NiSO_4.6H_2O$) (20 g/l), sodium acetate ($CH_3COONa$) (10 g/l) and sodium hypophosphite ($NaH_2PO_2$) (10 g/l) are added to 5 g of carrier $Z_1$, the mixture is stirred and heated to 363° K, maintained for 2 hours. The obtained solid product is washed with distilled water until free from acidic ions, and dried overnight at 340° K. The resulting Ni—P/$SiO_2$ amorphous alloy catalyst ($C_{27}$) contains 0.6 wt % of Ni, 0.07 wt % of P, in which the yield of Ni—P amorphous alloy supported is 20.1 wt %, and yield of Ni supported is 16.9 wt %, based on the total weight of the catalyst.

Comparative Example 2

Ni—P/SiO$_2$ amorphous alloy catalyst (C$_{28}$) available from Jingfa Deng, which is prepared according to the process disclosed in Appl. Catal. 37, 339–340, (1988), contains 11.70 wt % of Ni, based on the total weight of the catalyst, 1.30 wt % of P, based on the total weight of the catalyst and with the balance as SiO$_2$. Its specific surface area is 85 m$^2$/g.

Comparative Example 3

Preparation of comparative Ni—La—P amorphous alloy catalyst with high specific surface area.

Ni—La—P amorphous alloy catalyst (C$_{29}$) with high specific surface area is prepared according to example 6 in CN 1073726A. It contains 87.4 wt % of Ni, based on the total weight of the catalyst, 0.4 wt % of La, based on the total weight of the catalyst and 12.2 wt % of P, based on the total weight of the catalyst. Its specific surface area is 91 m$^2$/g.

Comparative Example 4

Preparation of comparative polycrystalline Ni catalyst

A polycrystalline Ni catalyst (No. C$_{30}$) is prepared according to the following steps: 5.0 g carrier Z$_1$ is impregnated by 9.82 g of a nickel nitrate solution, at a final nickel concentration of 8.35 wt %, based on the total weight of the catalyst. The sample is dried at 100° C. for 4 hour, and further calcined at 500° C. for 3 hours. Then it is reduced in a H$_2$ stream at 460° C. for 4 hours. The amount of the supported Ni is 5.0 wt %, based on the total weight of the catalyst, determined by ICP.

Examples 27–29

The following examples demonstrate the thermal stability of the catalysts according to the present invention.

Figure 5:
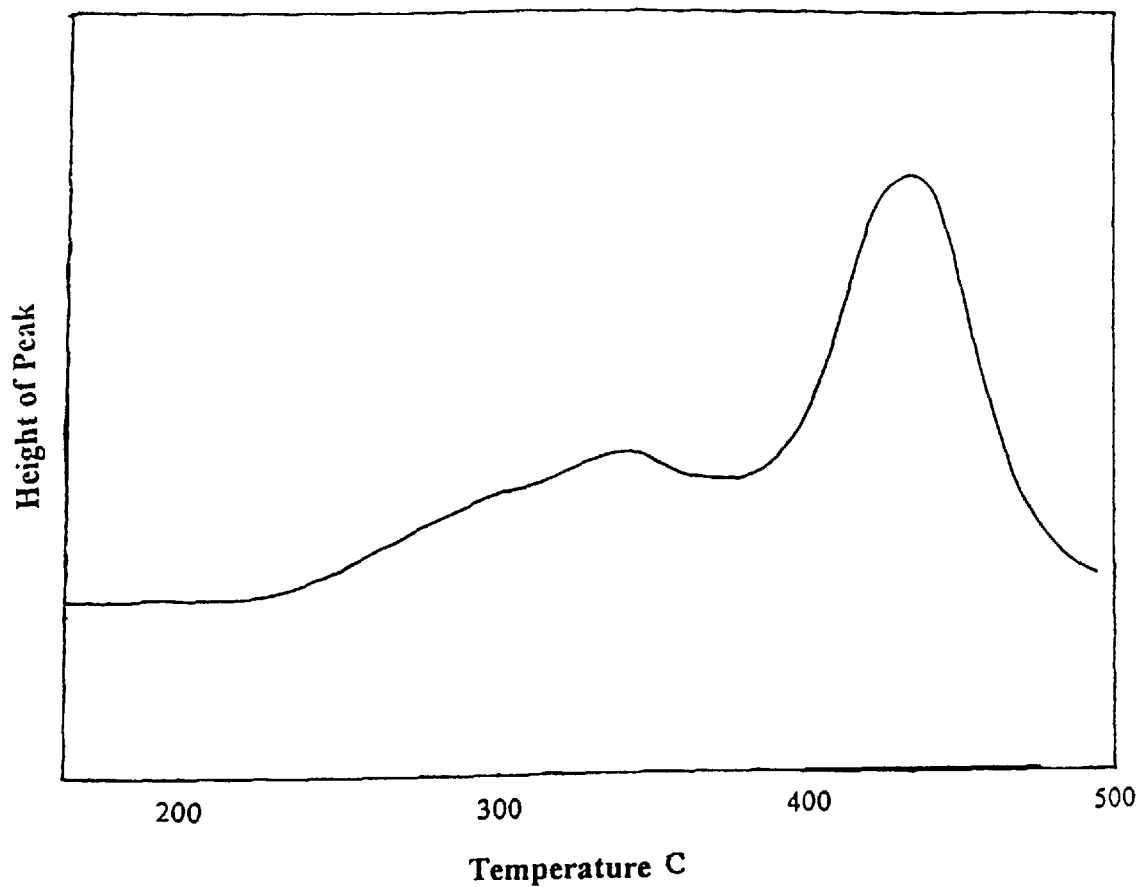
FIG. 5 shows the DSC curve of the catalysts containing Ni—P amorphous alloy using $SiO_2$ as the carrier according to the present invention.
Figure 6:
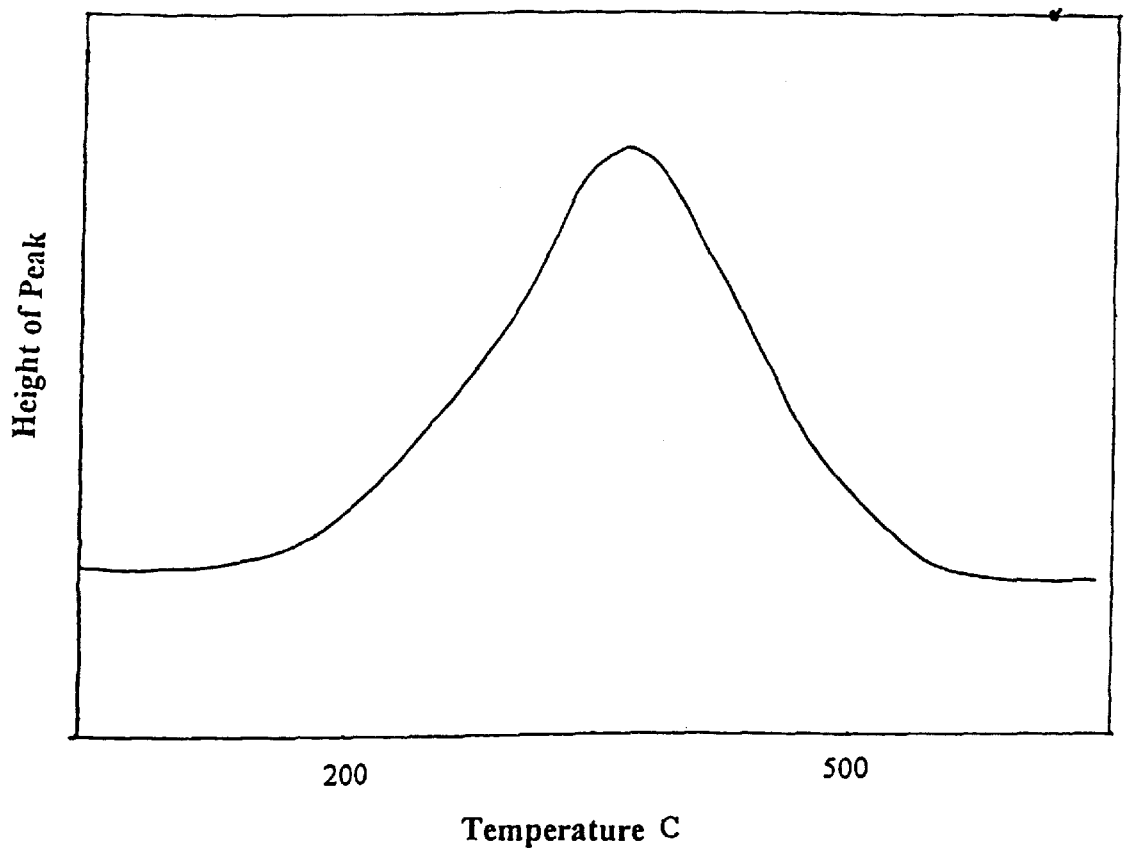
FIG. 6 shows the DSC curve of the catalysts containing Ni—P amorphous alloy using active carbon as the carrier according to the present invention.
Figure 7:
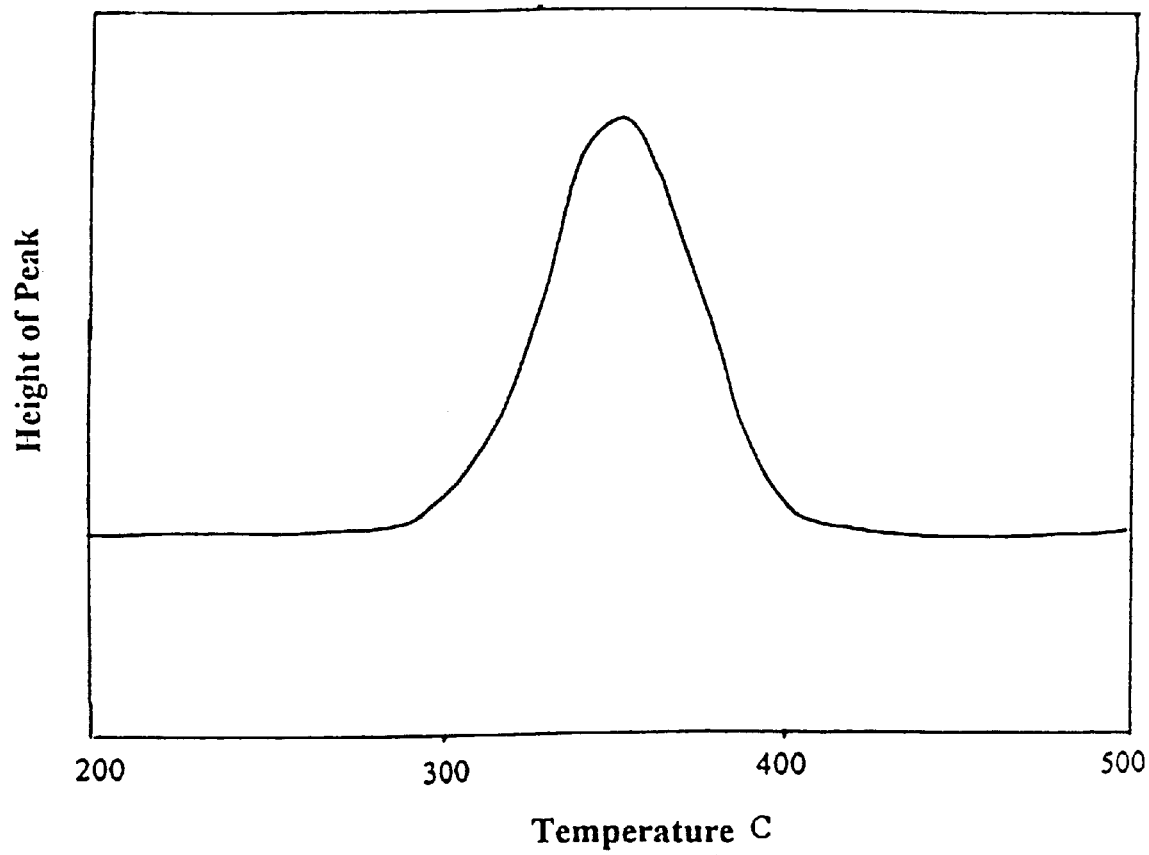
FIG. 7 shows the DSC curve of the catalysts containing Ni—P amorphous alloy using __-$Al_2O_3$ as the carrier according to the present invention.

Take 5.0 mg of each of the catalysts C$_5$, C$_{13}$ and C$_{14}$. The DSC curves and the maximal crystallization temperatures (Tc) are determined by DSC on a Du Pont 2 100 Thermal Analysis System in N$_2$ flow at the ramp of 10° C./min. Their DSC curves are shown in FIGS. 5–7.

Comparative Example 5

Figure 8:
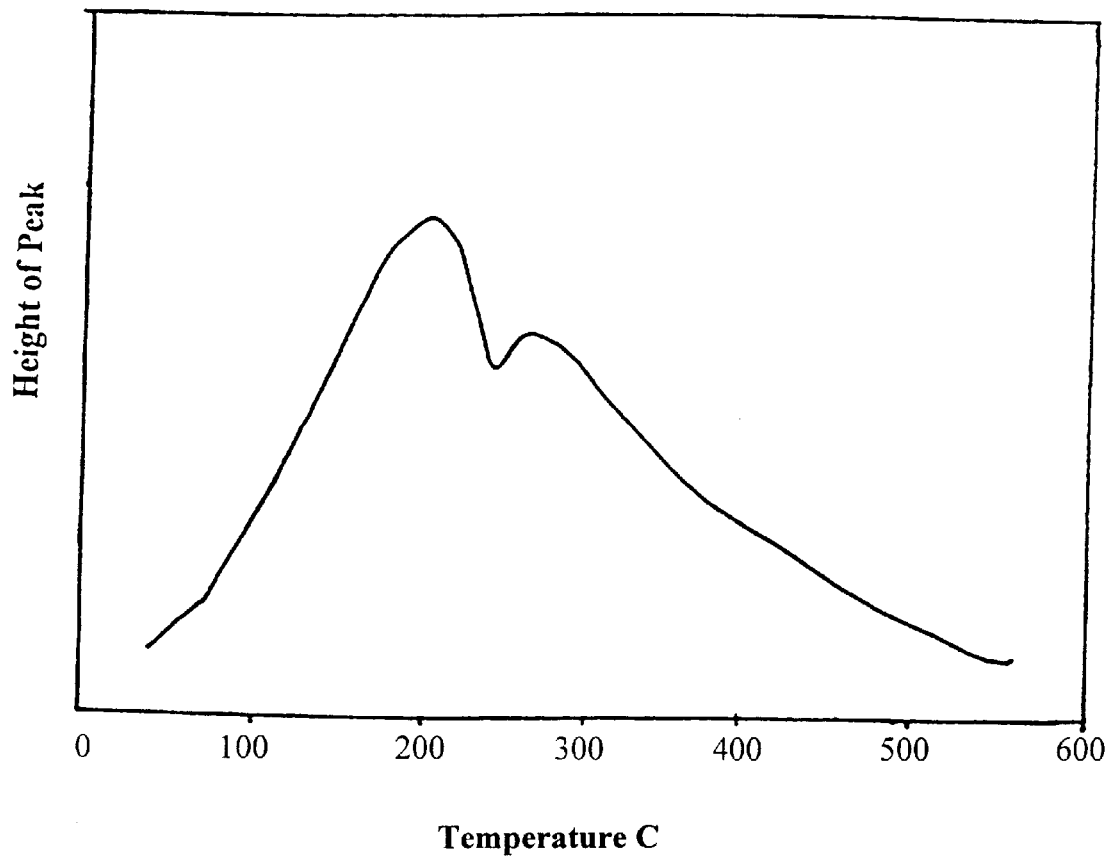
FIG. 8 shows the DSC curve of the catalysts containing Ni—La—P amorphous alloy with high specific surface area according to CN 1073726A.

Take 5.0 mg of catalyst C$_{29}$, The DSC curve is determined under conditions as indicated in examples 16–18, and its DSC curve is shown in FIG. 8.

Example 30–34

The following examples show the thermal stability of the catalysts according to the present invention.

Take 5.0 mg of each catalysts C$_{16}$–C$_{20}$. The DSC curves and the maximal crystallization temperatures (Tc) are determined by DSC on a Du Pont 2100 Thermal Analysis System in N$_2$ flow at the ramp of 10° C./min. The results are shown in Table 11.

Comparative Example 6

Take 5.0 mg of catalyst C$_{29}$, The DSC curve is determined using the same method and condition as indicated in examples 30–34, and the results are shown in Table 11.

TABLE 11

| Exp. No. | Catalyst No. | Tc (C) | Metal additive (M) |
|---|---|---|---|
| 30 | C$_{16}$ | 432 | Mo |
| 31 | C$_{17}$ | 431 | W |
| 32 | C$_{18}$ | 359 | Co |
| 33 | C$_{19}$ | 354 | Fe |
| 34 | C$_{20}$ | 395 | Cu |
| Compa. Exp. 6 | C$_{29}$ | 270 | La |

The results obtained from examples 27–34, and comparative examples 5–6, show that the inventive catalysts have superior thermal stability, their maximal crystallization temperature (Tc) is remarkably higher than that of the amorphous alloy catalyst with high specific surface area, and at least not lower than that of known Ni—P/SiO$_2$ amorphous alloy catalysts. These results also show that the crystallization of the inventive catalyst may have one or more phase transition(s) depending on property of the carriers, which is confirmed by the DSC curve having one or more phase transition peak(s).

The following examples and comparative examples demonstrate the uses and the reactivity of the catalysts of the present invention during hydrogenation of the compounds having various unsaturated functional groups.

Examples 35–37

The use and activity of the catalysts of the present invention during the selective hydrogenation of trace ethyne in ethylene.

Figure 9:
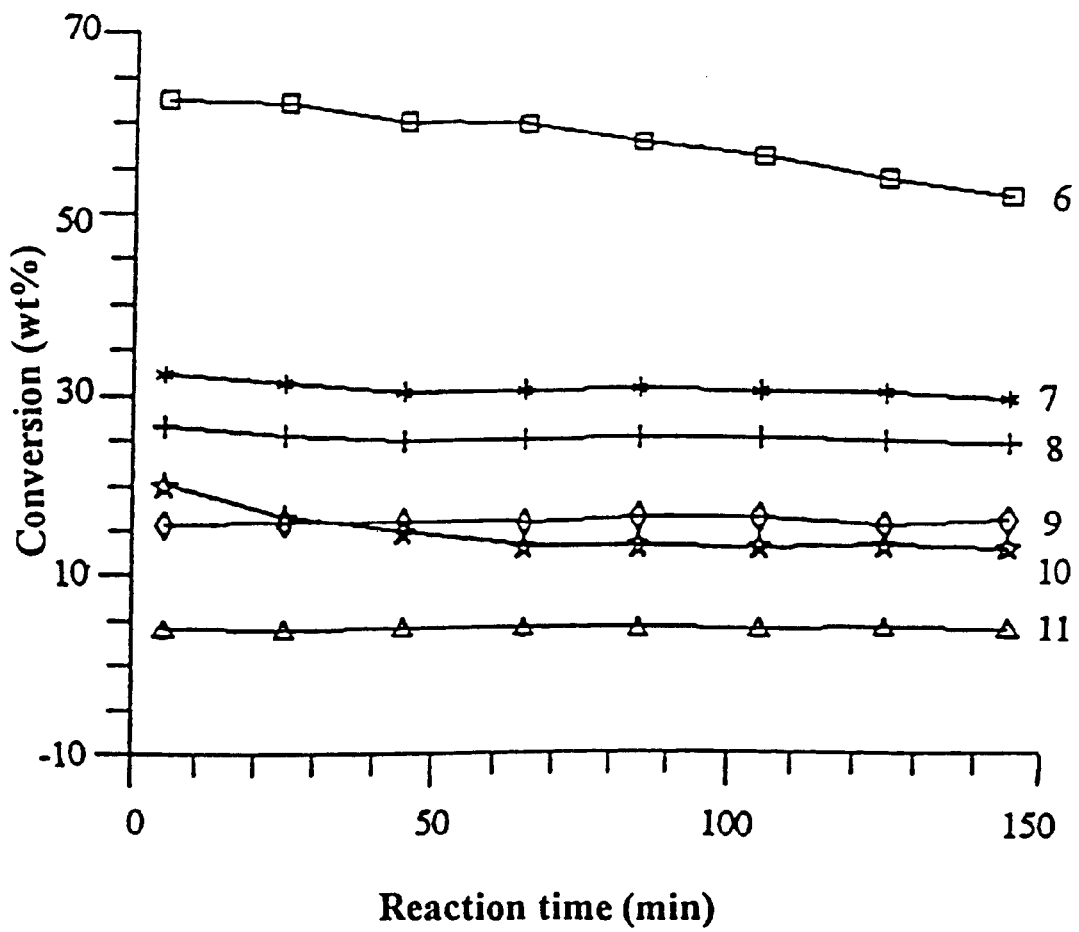
FIG. 9 shows the profile of the ethyne conversion vs. the reaction time during the selective hydrogenation of trace ethyne in ethylene using various catalysts.

The hydrogenation is carried out in a microreactor with a 3 mm I.D. and 2000 mm long. The catalysts employed are 0.04 g of each of C$_5$, C$_{13}$ and C$_{15}$. The composition of the feed gas is: ethyne 1.65 mol %, ethylene 95.79 mol %, and hydrogen 2.56 mol %. The reaction conditions are T=110° C., P=10.0 MPa, gas space velocity=9000 hour$^{-1}$. The composition of the feed gas and of products are analyzed on-line by gas chromatography(GC). The profiles of the ethyne conversion vs. reaction time are shown in FIG. 9 (plots 6, 7 and 8), corresponding to the catalysts C$_5$, C$_{13}$ and C$_{15}$, respectively.

Comparative Examples 7–9

The following comparative examples demonstrate that, the reactivity of the catalysts of the present invention is significantly higher than that of the prior art catalysts reported so far.

The reactor, raw materials and reaction conditions are the same as those given in examples 35–37, except that the catalysts used are C$_{28}$, C$_{29}$ and C$_{30}$. The profiles of the ethyne conversion vs. reaction time are shown in FIG. 9 (plots 9, 10, 11, respectively).

FIG. 9 shows that inventive catalysts have hydrogenation activity remarkably higher than that of the known polycrystalline Ni catalyst Ni—P/SiO$_2$, and the Ni—La—P amorphous alloy catalyst which has high specific surface area, and the highest catalytic activity known from the prior art so far. At the same time, the catalysts of the present invention have much lower contents of Ni than that of the known Ni—La—P amorphous alloy catalyst with high specific surface area, and thus are efficient catalysts with low Ni content.

Examples 38–40

The use of the catalysts of the present invention during the selective hydrogenation of trace ethyne in ethylene.

Figure 10:
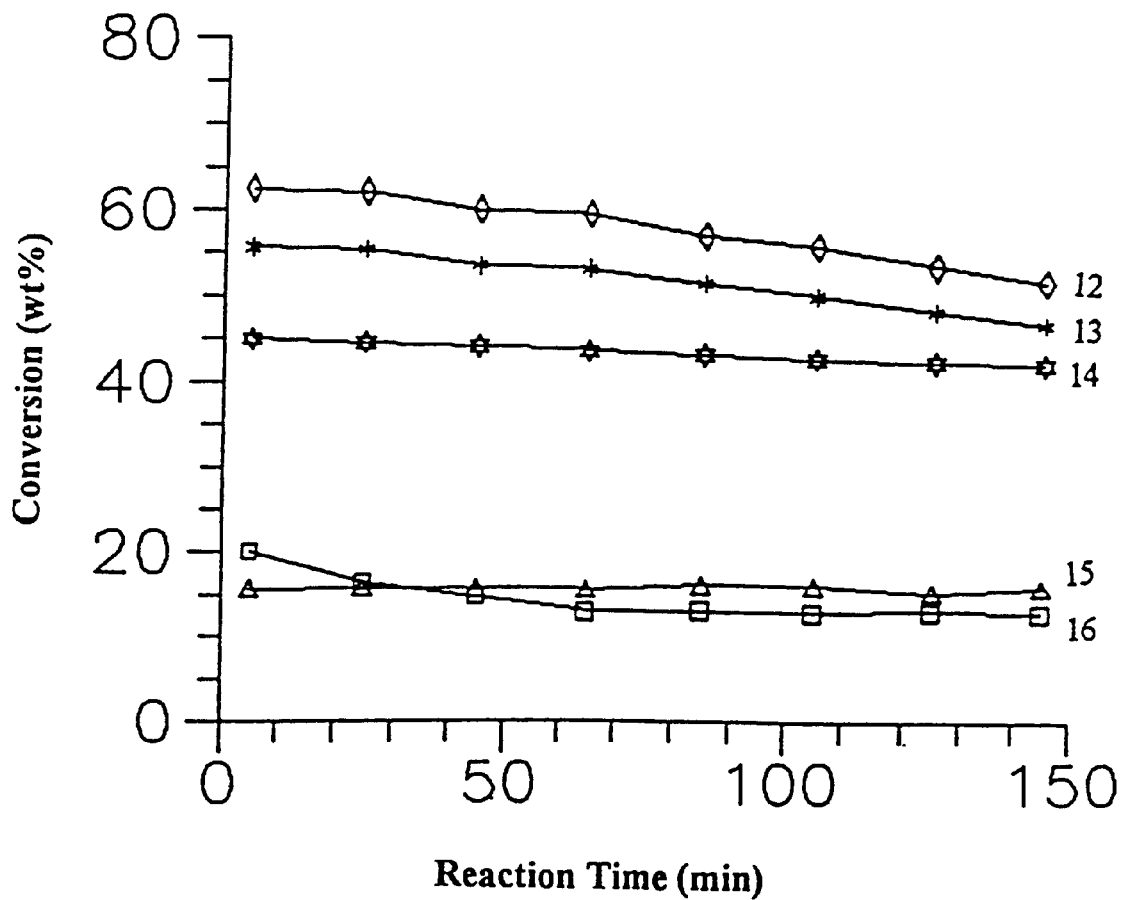
FIG. 10 shows the profile of the ethyne conversion vs. the reaction time during the selective hydrogenation of trace ethyne in ethylene using another group of catalysts.

The hydrogenation is carried out in a microreactor with a 3 mm I.D. and 2000 mm long. The catalysts employed are 0.04 g of $C_{18}$, $C_{19}$ or $C_{24}$. The composition of the feed gas is: ethyne 1.65 mol %, ethylene 95.79 mol %, and hydrogen 2.56 mol %. The reaction conditions are T=110° C., P=10.0 MPa, gas space velocity=9000 hour$^{-1}$, The composition of the feed gas and of products are analyzed on-line by a gas chromatography (GC). The profiles of the ethyne conversion vs. reaction time are shown in FIG. 10 (plots 12, 13 and 14), corresponding to the catalyst $C_{18}$, $C_{19}$ and $C_{24}$, respectively.

Comparative Examples 10–11

The following comparative examples demonstrate that, during the selective hydrogenation of trace ethyne in ethylene, the hydrogenation activity of the catalysts of the present invention is significantly higher than that of the prior art amorphous alloy catalysts reported.

The reactor, raw materials and reaction conditions are the same as those given in examples 38–40, except that the catalysts used are catalysts $C_{28}$, and $C_{29}$. The profiles of the ethyne conversion vs. reaction time are shown in FIG. 10 (plots 15, 16, respectively).

Examples 41–42

The use of the catalysts of the present invention during the hydrogenation of toluene into methylcyclohexane.

The reaction is performed in a 100 ml autoclave containing 50 ml 20 wt % of toluene dissolved in cyclohexane, and 0.2 g of catalyst $C_5$ or $C_{18}$. The autoclave is filled with $H_2$ to 4.0 MPa, and heated to 140° C. The reaction is started by stirring the reaction mixture at a rate of 64 rpm. After a reaction for 1.0 hour, the reaction mixture is cooled and taken out, and analyzed on-line by a GC. The results are shown in Table 12.

TABLE 12

| Exp. No. | Catalyst No. | Conversion of toluene, wt % |
|---|---|---|
| 41 | $C_5$ | 2.46 |
| 42 | $C_{18}$ | 3.10 |

Examples 43–46

The use of the catalysts of the present invention during the hydrogenation of styrene into ethylbenzene.

The hydrogenation is carried out in the same way as that used in examples 41–42. The reaction conditions are: 50 ml styrene, 0.2 g catalyst, temperature is 60° C. or 130° C., and the reaction time is 0.5 hour. The other steps are the same as those given in examples 41–42. The results are shown in Table 13.

TABLE 13

| Exp. No. | Reaction temperature, ° C. | Catalyst | Conversion of styrene, wt % |
|---|---|---|---|
| 43 | 60 | $C_5$ | 0.22 |
| 44 | 130 | $C_5$ | 91.01 |
| 45 | 60 | $C_{18}$ | 0.41 |
| 46 | 130 | $C_{18}$ | 94.32 |

Example 47–48

The use of the catalysts of the present invention during the hydrogenation of hexanedinitrile into hexanediamine.

The hydrogenation is carried out in the same way as that used in examples 41–42. The reaction conditions are: 50 ml of 15 wt % of hexanedinitrile in ethanol, temperature is 100° C., reaction time is 1 hour. The results are shown in Table 14.

TABLE 14

| Exp. No. | Catalyst | Conversion of hexanedinitrile, wt % |
|---|---|---|
| 47 | $C_5$ | 1.49 |
| 48 | $C_{18}$ | 3.10 |

Examples 49–50

The use of the catalysts of the present invention during the hydrogenation of nitrobenzene into aniline.

The hydrogenation is carried out in the same way as that used in examples 41–42. The reaction conditions are: 50 ml of 20 wt % of nitrobenzene in isopropanol, reaction temperature is 89° C., reaction time 1 hour. The other steps are the same as those given in examples 41–42. The result is shown in Table 15.

TABLE 15

| Exp. No. | Catalyst | Conversion of nitrobenzene, wt % |
|---|---|---|
| 49 | $C_5$ | 1.41 |
| 50 | $C_{18}$ | 2.19 |

Examples 51–52

The use of the catalysts of the present invention during the hydrogenation of cyclohexanone into cyclohexanol.

The hydrogenation is carried out in the same way as that used in examples 41–42. The reaction conditions are following: 50 ml 30 wt % of cyclohexanone in cyclohexane, reaction temperature is 95° C., reaction time is 1 hour. The other steps are the same as those given in examples 41–42. The result is shown in Table 16.

TABLE 16

| Exp. No. | Catalyst | Conversion of cyclohexanone, wt % |
|---|---|---|
| 51 | $C_5$ | 0.46 |
| 52 | $C_{18}$ | 0.73 |

Examples 53–54

The use of the catalysts of the present invention during the hydrogenation of ethynylbenzene into styrene.

The hydrogenation is carried out in the same way as that used in examples 41–42. The reaction conditions are following: 50 ml 15 wt % of ethynylbenzene in cyclohexane, 0.2 g catalyst, reaction temperature is 22° C., reaction time is 0.5 hour. The other steps are the same as those given in examples 41–42. The result is shown in Table 17.

TABLE 17

| Exp No. | Catalyst | Conversion, wt % | Selectivity, mole % |
|---|---|---|---|
| 53 | $C_5$ | 4.13 | 100 |
| 54 | $C_{18}$ | 6.01 | 100 |

Selectivity of styrene=content of styrene in product/(content of styrene in product+content of ethylbenzene in product)× 100%

We claim:

1. A supported amorphous alloy catalyst containing nickel and phosphorus, wherein said catalyst comprises a porous carrier, a Ni—P amorphous alloy supported on the carrier, and a catalytic component which has been pre-supported on the carrier for inducing and catalyzing the formation of the said Ni—P amorphous alloy onto the carrier wherein said catalytic component is an amorphous alloy of one or more metals with boron. wherein the metal or metals are selected from Group VIII of the Elemental Periodic System; and wherein the contents of the nickel, phosphorous and the catalytic components are 0.15–30 wt %, 0.03–10 wt %, and 0.01–10 wt %, respectively, based on the total weight of the catalyst.

2. A catalyst according to claim 1, wherein the said catalytic component is selected from Fe—B, Co—B and Ni—B amorphous alloy.

3. A catalyst according to claim 1, wherein said catalytic component is 0.01–5 wt %, based upon the total weight of the catalyst.

4. A catalyst according to claim 1, wherein said pre-supported catalytic component is a Ni—B amorphous alloy.

5. A catalyst according to claim 4, wherein said catalyst comprises 0.15–30 wt % of Ni, 0.03–10 wt % of P, and 0.01–3.5 wt % of B, wherein the atomic ratio Ni/P in said Ni—P amorphous alloy is from 0.5 to 10, and the atomic ratio Ni/B in said Ni—B amorphous alloy is from 0.5 to 10.

6. A catalyst according to claim 5, wherein said catalyst comprises 0.5–20 wt % of Ni, 0.1–5 wt % of P, and 0.02–2 wt % of B, respectively, based on the total weight of the catalyst.

7. A catalyst according to claim 6, wherein said catalyst comprises 1–15 wt % of Ni, 0.1–2.5 wt % of P, and 0.02–1 wt % of B, respectively, based on the total weight of the catalyst.

8. A catalyst according to claim 5, wherein the atomic ratio Ni/P in said Ni—P amorphous alloy is 1–5, and the atomic ratio Ni/B in said Ni—B amorphous alloy is 0.5–5.

9. A catalyst according to claim 4, wherein said catalyst further comprises from 0.01 to 20 wt % of a metal additive (M), based on the total weight of the catalyst, wherein said metal additive (M) refers to one or more metal elements, with the exception of Ni, which can be reduced from the corresponding salts into its elemental form by a solution containing $H_2PO_2^-$, wherein said metal additive (M) is present in the form of Ni—M—P amorphous alloy or in the form of a mixture of Ni—P amorphous alloy with a polycrystalline metal additive(M).

10. A catalyst according to claim 9, wherein the atomic ratio (Ni+M)/P is from 0.5 to 10, and the atomic ratio Ni/M is from 0.1 to 1000 in said Ni—M—P amorphous alloy or in said mixture of Ni—P amorphous alloy with a polycrystalline metal additive (M).

11. A catalyst according to claim 9, wherein the atomic ratio (Ni+M)/P is from 1 to 6, the atomic ratio Ni/M is from 1 to 700 in said Ni—M—P amorphous alloy or in said mixture of Ni—P amorphous alloy with the polycrystalline metal additive (M), and the atomic ratio Ni/B is from 1 to 5 in said Ni—B amorphous alloy.

12. A catalyst according to claim 9, wherein said catalyst comprises 0.5–20 wt % of Ni, 0.1–5 wt % of P, and 0.02–2 wt % of B, 0.01–10 wt % of metal additive (M), respectively based on the total weight of the catalyst.

13. A catalyst according to claim 12, wherein said catalyst comprises 1–15 wt % of Ni, 0.1–2.5 wt % of P, and 0.02–1 wt % of B, 0.01–5 wt % of metal additive (M), respectively, based on the total weight of the catalyst.

14. A catalyst according to claim 1, wherein said porous carrier is selected from porous inorganic oxides, active carbon, zeolite, molecular sieve or a mixture comprising two or more thereof.

15. A catalyst according to claim 14, wherein said porous carrier is selected from silica, active carbon or alumina.

16. A catalyst according to claims 1 or 9, wherein the specific surface area of the catalyst is from 100 to 1000 $m^2$/g.

17. A catalyst according to claim 9, wherein said metal additive is selected from one or more metal elements of Groups IB, VIB, and VIII but excluding Ni.

18. A catalyst according to claim 17, wherein said metal additive is one or more metal elements selected from the group comprising Fe, Co, Cu, Mo, and W.

19. A process for preparation of the catalyst as claimed in claim 1, wherein the process comprises:

(1) contacting the porous carrier pre-supported with the metal ions of the catalytic component with a solution containing $BH_4^-$ at a temperature between the melting-point of the solution and 100° C., thereby reducing said pre-supported metal ion of the catalytic component into the pre-supported catalytic component; and (2) contacting the porous carrier pre-supported with the catalytic component with a mixed solution containing $H<PO_2^-$ and $Ni^{2+}$ at a temperature between the melting point of the solution and 100° C. so as to form the Ni—P amorphous alloy on the porous carrier.

20. A process according to claim 19, wherein the said metal ion of the catalytic component is $Ni^{2+}$, said catalytic component is a Ni—B amorphous alloy, and said porous carrier pre-supported with the catalytic component is a porous carrier pre-supported with a Ni—B amorphous alloy.

21. A process according to claim 20, wherein the porous carrier containing 0.1–20 wt % of $Ni^{2+}$ is contacted with a solution containing 0.5–10M $BH_4^-$ wherein the atomic ratio B/Ni is 0.1–10, whereby a porous carrier pre-supported with 0.1–20 wt % of Ni—B amorphous alloy, based on the total weight of the catalyst, and having an atomic ratio Ni/B of 0.5–10 results; contacting said porous carrier pre-supported with Ni—B amorphous alloy with a mixed solution-containing $H_2PO_2^-$ and $Ni^{2+}$ each at a concentration of 0.01–5 M, and with the atomic ratio P/Ni being above 0.5, wherein the weight ratio of said porous carrier containing Ni—B amorphous alloy to $Ni^{2+}$ contained in said solution is in range of 1000–1.

22. A process according to claim 19, wherein said mixed solution containing $H_2PO_2^-$ and $Ni^{2+}$ further contains a metal additive ion.

23. A process according to claim 22, wherein said mixed solution containing $H_2PO_2^-$, $Ni^{2+}$ and metal additive (M) ion has an atomic ratio P/(Ni+M) of at least 0.5.

24. A process according to claim 23, wherein said mixed solution contains $H_2PO_2^-$, $Ni^{2+}$ and metal additive (M) ion at molar concentrations of $H_2PO_2^-$, $Ni^{2+}$ and metal additive ion of 0.01–5.0, 0.01–5.0 and 0.01–3.0, respectively.

25. A process according to claim 23, wherein said atomic ratio P/(Ni+M) is at least 1.0.

26. A process according to claim 25, wherein said atomic ratio P/(Ni+M) is in the range of 3–7.

27. A process according to claim 22, wherein said metal additive ion is selected from one or more ions of the metal elements of group IB, VIB, and VIII but excluding Ni.

28. A process according to claim 27, wherein said metal additive ion is selected from one or more of $Fe^{2+}$, $Co^{2+}$, $Cu^{2+}$, $MoO_4^{2-}$, $WO_4^{2-}$, or metatungstate.

29. A process according to claim 27, wherein the precursor of said metal additive ion is selected from soluble salts of said metal additive.

30. A process according to claim 20, wherein said solution containing $BH_4^-$ is an aqueous solution containing $BH_4^-$, wherein the $BH_4^-$ ion is obtained from a precursor selected from the group consisting of $KBH_4$, $NaBH_4$ or a mixture thereof, said porous carrier containing 0.8–8 wt % of Ni, based on the total weight of the catalyst; and the temperature for contacting the porous carrier containing Ni with said solution containing $BH_4^-$ is between room temperature and 50° C.

31. A process according to claim 20, wherein said porous carrier containing Ni—B contains 0.5–8 wt % of Ni—B amorphous alloy with the atomic ratio Ni/B in the range of 1–5.

32. A process according to claim 20, wherein said solution containing $H_2PO_2^-$ and $Ni^{2+}$ is an aqueous solution containing $H_2PO_2^-$ and $Ni^{2+}$.

33. A process according to claim 19, wherein $H_2PO_2^-$ is obtained from a precursor selected from the group consisting of $KH_2PO_2^-$, $NaH_2PO_2^-$ or a mixture thereof; and the precursor of $Ni^{2+}$ is selected from soluble Ni salts.

34. A process according to claim 33, wherein $Ni^{2+}$ is obtained from a precursor selected from; $NiCl_2$, or $NiAc_2$.

35. A process according to claim 20, wherein said mixed solution containing $H_2PO_2^-$ and $Ni^{2+}$ has an atomic ratio P/Ni of above 1.

36. A process according to claim 35, wherein said atomic ratio P/Ni is in the range of 4–7.

37. A process according to claim 20, wherein the weight ratio of said porous carrier containing Ni—B amorphous alloy to $Ni^{2+}$ in said mixing solution is in the range of 5–200.

38. A process according to claim 37, wherein the weight ratio of said porous carrier containing Ni—B amorphous alloy to $Ni^{2+}$ in said solution is in the range of 5–100.

39. A process according to claim 20, wherein said porous carrier containing Ni—B amorphous alloy is mixed directly with said solution containing $H_2PO_2^-$ and $Ni^{2+}$ under agitation.

* * * * *

UNITED STATES PATENT AND TRADEMARK OFFICE
CERTIFICATE OF CORRECTION

PATENT NO. : 6,051,528

DATED : APRIL 18, 2000

INVENTOR(S) : Ma, et al.

It is certified that error appears in the above-identified patent and that said Letters Patent is hereby corrected as shown below:

| | |
|---|---|
| Col. 9, line 47: | Change "using __-Al$_2$O$_3$" to -- using $\delta$-Al$_2$O$_3$ -- |
| Col. 10, line 8: | Change "the __-Al$_2$O$_3$" to -- the $\delta$-Al$_2$O$_3$ -- |
| Col. 10, line 12: | Change "the __-Al$_2$O$_3$" to -- the $\gamma$-Al$_2$O$_3$ -- |
| Col. 10, Table 2: | Change "W$_{JBH4}$" to -- W$_{KBH4}$ -- |
| Col. 12, line 30: | Change "CuK__" to -- CuK $\propto$ -- |
| Col. 13-14, Table 7, Col. 7: | Change "C$_{NAH2PO2}$" to -- C$_{NaH2PO2}$ -- |
| Col. 15-16, Table 8, Col. 7: | Change "C$_{NAH2PO2}$" to -- C$_{NaH2PO2}$ -- |
| Col. 16, line 30: | Change "339340" to -- 339-340 -- |
| Col. 16, line 55: | Change "CuK__" to -- CuK $\propto$ -- |
| Col. 16, line 61: | Change "CuK__" to -- CuK $\propto$ -- |
| Col. 16, line 67: | Change "__-Al$_2$O$_3$ or __-Al$_2$O$_3$" to -- $\delta$-Al$_2$O$_3$ or $\gamma$-Al$_2$O$_3$ -- |

UNITED STATES PATENT AND TRADEMARK OFFICE
CERTIFICATE OF CORRECTION

PATENT NO. : 6,051,528

DATED : APRIL 18, 2000

INVENTOR(S) : Ma, et al.

It is certified that error appears in the above-identified patent and that said Letters Patent is hereby corrected as shown below:

Col. 5, line 25: Change "2θ=450" to -- $2\theta=45°$ --

Col. 22, line 35, Claim 19: Change "H<PO$_2^-$" to -- $H_2PO_2^-$ --

Signed and Sealed this

Twenty-second Day of May, 2001

Attest:

NICHOLAS P. GODICI

Attesting Officer

Acting Director of the United States Patent and Trademark Office